US009102953B2

(12) United States Patent
Downey et al.

(10) Patent No.: US 9,102,953 B2
(45) Date of Patent: *Aug. 11, 2015

(54) BIOGASIFICATION OF COAL TO METHANE AND OTHER USEFUL PRODUCTS

(75) Inventors: Robert A. Downey, Centennial, CO (US); Song Jin, Fort Collins, CO (US); Paul H. Fallgren, Highlands Ranch, CO (US)

(73) Assignee: Ciris Energy, Inc., Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,285

(22) Filed: Dec. 10, 2010

(65) Prior Publication Data

US 2011/0151533 A1 Jun. 23, 2011

Related U.S. Application Data

(60) Provisional application No. 61/329,862, filed on Apr. 30, 2010, provisional application No. 61/284,483, filed on Dec. 18, 2009.

(51) Int. Cl.
*C12P 5/02* (2006.01)
*C12M 1/107* (2006.01)
*C12M 1/00* (2006.01)

(52) U.S. Cl.
CPC ............. *C12P 5/023* (2013.01); *C12M 21/04* (2013.01); *C12M 45/04* (2013.01); *Y02E 50/343* (2013.01)

(58) Field of Classification Search
USPC ........................................................ 435/167
See application file for complete search history.

(56) References Cited

U.S. PATENT DOCUMENTS

| 1,606,015 | A | 11/1926 | Blackwell |
| 2,992,093 | A | 7/1961 | Burdick ............................ 71/24 |
| 3,076,291 | A | 2/1963 | Gardner ............................ 47/58 |
| 3,111,404 | A | 11/1963 | Karcher et al. ................... 71/24 |
| 3,264,064 | A | 8/1966 | Natta ............................ 23/203 |
| 3,352,902 | A | 11/1967 | Moschopedas ............... 260/507 |
| 3,398,186 | A | 8/1968 | Schwartz ..................... 260/515 |
| 3,418,100 | A | 12/1968 | Cooley ............................ 71/24 |
| 3,544,295 | A | 12/1970 | Nakamigawa et al. ............. 71/1 |
| 3,574,649 | A | 4/1971 | Fanti et al. .................... 117/106 |
| 3,607,211 | A | 9/1971 | Cole et al. .......................... 71/1 |
| 3,640,846 | A | 2/1972 | Johnson |
| 3,674,649 | A | 7/1972 | Formisano et al. ........... 195/104 |

(Continued)

FOREIGN PATENT DOCUMENTS

| EP | 1788080 | 5/2007 |
| JP | 57147596 A | 9/1982 |

(Continued)

OTHER PUBLICATIONS

Ahmed, et al., Advanced Reservoir Engineering, Gulf Professional Publishing (Elsevier), p. 3/226 (2004).

(Continued)

*Primary Examiner* — Jon P Weber
*Assistant Examiner* — Kara Johnson
(74) *Attorney, Agent, or Firm* — Mendelsohn, Drucker & Dunleavy, P.C.

(57) ABSTRACT

Method of bioconversion of coal to methane, carbon dioxide, and other valuable gaseous and liquid products in a multi-step process that may include particle size reduction, separation of non-coal materials, addition of chemicals, and multi-stage anaerobic fermentation are disclosed.

32 Claims, 7 Drawing Sheets

(56) References Cited

U.S. PATENT DOCUMENTS

| | | | | |
|---|---|---|---|---|
| 3,711,392 | A | 1/1973 | Metzger | 204/180 |
| 3,744,566 | A | 7/1973 | Szabo et al. | 166/275 |
| 3,770,411 | A | 11/1973 | Chambers et al. | 71/24 |
| 3,826,308 | A | 7/1974 | Compere-Whitney | |
| 3,965,985 | A | 6/1976 | Hitzman | |
| 3,973,628 | A * | 8/1976 | Colgate | 166/283 |
| 3,981,803 | A | 9/1976 | Coulthard | 210/178 |
| 3,982,998 | A | 9/1976 | Hitzman et al. | |
| 3,990,513 | A | 11/1976 | Perch | 166/267 |
| 4,007,789 | A | 2/1977 | Clampitt | 166/281 |
| 4,010,098 | A | 3/1977 | Fassell | |
| 4,021,329 | A | 5/1977 | Seitzer | 208/10 |
| 4,033,852 | A | 7/1977 | Horowitz | |
| 4,110,193 | A | 8/1978 | Gwyn et al. | |
| 4,120,665 | A | 10/1978 | Kindig et al. | |
| 4,151,068 | A | 4/1979 | McCollum et al. | |
| 4,206,288 | A | 6/1980 | Detz et al. | 435/267 |
| 4,257,869 | A | 3/1981 | Dickert et al. | 208/8 |
| 4,259,084 | A | 3/1981 | Liotta | 44/1 |
| 4,261,420 | A | 4/1981 | Hitzman | |
| 4,274,760 | A | 6/1981 | Norman | 405/163 |
| 4,298,450 | A | 11/1981 | Ross et al. | 208/8 |
| 4,298,621 | A | 11/1981 | Samis et al. | 426/55 |
| 4,319,041 | A | 3/1982 | Goff | 562/475 |
| 4,321,076 | A | 3/1982 | Firth, Jr. | 71/24 |
| 4,331,447 | A | 5/1982 | Kamada et al. | |
| 4,358,537 | A | 11/1982 | Chynoweth | |
| 4,366,073 | A | 12/1982 | McLaughlin | 252/8.55 R |
| 4,394,136 | A | 7/1983 | Grabis | 48/111 |
| 4,397,953 | A | 8/1983 | Guazzone et al. | 435/243 |
| 4,400,195 | A | 8/1983 | Rijkens | 71/10 |
| 4,425,219 | A | 1/1984 | Kroo et al. | |
| 4,428,820 | A | 1/1984 | Kuehler et al. | |
| 4,436,818 | A | 3/1984 | Widmer | 435/316 |
| 4,451,351 | A | 5/1984 | Porter et al. | 208/10 |
| 4,501,445 | A | 2/1985 | Gregoli | 299/2 |
| 4,539,094 | A | 9/1985 | Sunder et al. | |
| 4,541,914 | A | 9/1985 | Hirokoh et al. | 208/10 |
| 4,556,430 | A | 12/1985 | Converse et al. | |
| 4,613,434 | A | 9/1986 | Maatta | 210/151 |
| 4,632,692 | A | 12/1986 | Lebesgue et al. | 71/10 |
| 4,647,537 | A | 3/1987 | Shigemitsu | 435/178 |
| 4,654,308 | A | 3/1987 | Safi et al. | 435/310 |
| 4,659,670 | A | 4/1987 | Stevens, Jr. et al. | 435/262 |
| 4,671,801 | A | 6/1987 | Burgess et al. | |
| 4,675,294 | A | 6/1987 | Finck et al. | 435/167 |
| 4,728,418 | A | 3/1988 | Shabtai et al. | 208/413 |
| 4,731,179 | A | 3/1988 | De Baere | 210/251 |
| 4,735,706 | A | 4/1988 | Ruether | 208/426 |
| 4,775,627 | A | 10/1988 | Attia et al. | 435/262 |
| 4,787,456 | A | 11/1988 | Jennings et al. | 166/281 |
| 4,798,801 | A | 1/1989 | Hitzman | 435/313 |
| 4,826,769 | A | 5/1989 | Menger | |
| 4,845,034 | A | 7/1989 | Menger et al. | 435/167 |
| 4,846,963 | A | 7/1989 | Knudson et al. | 208/408 |
| 4,861,519 | A | 8/1989 | Tusa et al. | 252/633 |
| 4,882,274 | A | 11/1989 | Pyne, Jr. et al. | 435/68 |
| 4,883,753 | A | 11/1989 | Belaich et al. | |
| 4,891,131 | A | 1/1990 | Sadeghi et al. | |
| 4,914,024 | A | 4/1990 | Strandberg et al. | 435/41 |
| 4,948,509 | A | 8/1990 | Stack | 210/603 |
| 4,985,060 | A | 1/1991 | Higa | 71/6 |
| 4,997,202 | A | 3/1991 | Kitagawa et al. | 280/719 |
| 5,009,340 | A | 4/1991 | Morane | 222/94 |
| 5,014,785 | A | 5/1991 | Puri et al. | 166/263 |
| 5,026,416 | A | 6/1991 | Alexander | 71/24 |
| 5,034,045 | A | 7/1991 | Alexander | 71/24 |
| 5,047,070 | A | 9/1991 | Harandi et al. | |
| 5,091,315 | A | 2/1992 | McCarty et al. | 435/287 |
| 5,120,430 | A | 6/1992 | Morgan | 208/428 |
| 5,179,021 | A | 1/1993 | du Manoir et al. | |
| 5,180,494 | A | 1/1993 | Yamaguchi et al. | 210/603 |
| 5,182,199 | A | 1/1993 | Hartley | 435/162 |
| 5,207,911 | A | 5/1993 | Pellegrin et al. | 210/603 |
| 5,282,879 | A | 2/1994 | Baccarani | 71/10 |
| 5,294,349 | A | 3/1994 | Kramer et al. | 208/400 |
| 5,298,163 | A | 3/1994 | Ehlinger | 210/603 |
| 5,327,964 | A | 7/1994 | O'Donnell et al. | |
| 5,340,376 | A | 8/1994 | Cunningham | |
| 5,350,684 | A | 9/1994 | Nakatsugawa et al. | |
| 5,363,913 | A | 11/1994 | Jennenman et al. | 166/246 |
| 5,389,258 | A | 2/1995 | Smis et al. | 210/603 |
| 5,424,195 | A | 6/1995 | Volkwein | 435/34 |
| 5,447,208 | A | 9/1995 | Lund et al. | 175/428 |
| 5,447,850 | A | 9/1995 | McCann | 435/42 |
| 5,486,214 | A | 1/1996 | Paszczynski et al. | 8/524 |
| 5,490,634 | A | 2/1996 | Jain et al. | 241/1 |
| 5,494,108 | A | 2/1996 | Palmer et al. | |
| 5,505,839 | A | 4/1996 | Suzuki et al. | |
| 5,523,234 | A | 6/1996 | Fichet | 435/289 |
| 5,560,737 | A | 10/1996 | Schuring et al. | 405/128 |
| 5,566,756 | A | 10/1996 | Chaback et al. | 166/263 |
| 5,597,714 | A | 1/1997 | Farone et al. | |
| 5,605,198 | A | 2/1997 | Tibbitts et al. | 175/432 |
| 5,612,493 | A | 3/1997 | Alexander | |
| 5,653,300 | A | 8/1997 | Lund et al. | 175/428 |
| 5,669,444 | A | 9/1997 | Riese et al. | |
| 5,670,345 | A | 9/1997 | Srivastava et al. | 435/75 |
| 5,773,526 | A | 6/1998 | Van Dijk et al. | 210/603 |
| 5,787,022 | A | 7/1998 | Tibbitts et al. | 364/578 |
| 5,792,355 | A | 8/1998 | Desjardins | 210/605 |
| 5,854,032 | A | 12/1998 | Srivastava et al. | 435/75 |
| 5,919,696 | A | 7/1999 | Ikeda et al. | |
| 5,950,747 | A | 9/1999 | Tibbitts et al. | 175/432 |
| 5,964,290 | A | 10/1999 | Riese et al. | |
| 5,967,233 | A | 10/1999 | Riese et al. | |
| 5,967,250 | A | 10/1999 | Lund et al. | 175/428 |
| 6,021,859 | A | 2/2000 | Tibbitts et al. | 175/431 |
| 6,043,392 | A | 3/2000 | Holtzapple et al. | 562/513 |
| 6,090,593 | A | 7/2000 | Fleming et al. | |
| 6,143,534 | A * | 11/2000 | Menger et al. | 435/167 |
| 6,145,608 | A | 11/2000 | Lund et al. | 175/428 |
| 6,156,946 | A | 12/2000 | Coyle et al. | |
| 6,180,396 | B1 | 1/2001 | Ono et al. | 435/289 |
| 6,210,955 | B1 | 4/2001 | Hayes | |
| 6,262,313 | B1 | 7/2001 | Holtzapple et al. | 568/397 |
| 6,338,390 | B1 | 1/2002 | Tibbitts | 175/56 |
| 6,342,378 | B1 | 1/2002 | Zhang et al. | 435/168 |
| 6,368,849 | B1 | 4/2002 | Norddahl | 435/262 |
| 6,423,532 | B1 | 7/2002 | Rindelaub | 435/262.5 |
| 6,440,307 | B1 | 8/2002 | Philip et al. | 210/617 |
| 6,543,535 | B2 | 4/2003 | Converse et al. | |
| 6,555,350 | B2 | 4/2003 | Ahring et al. | 435/162 |
| 6,571,874 | B1 | 6/2003 | Lovenich et al. | |
| 6,588,503 | B2 | 7/2003 | Karanikas et al. | |
| 6,679,326 | B2 | 1/2004 | Zakiewicz | 166/272.5 |
| 6,752,210 | B2 | 6/2004 | de Rouffignac et al. | |
| 6,773,596 | B2 | 8/2004 | Penzes et al. | 210/605 |
| 6,814,141 | B2 | 11/2004 | Huh et al. | 166/249 |
| 6,814,992 | B2 | 11/2004 | Pazik et al. | 426/231 |
| 6,817,411 | B2 | 11/2004 | Mones | |
| 6,852,226 | B2 | 2/2005 | Hiro et al. | 210/603 |
| 6,905,601 | B2 | 6/2005 | De Baere et al. | 210/603 |
| 7,015,028 | B2 | 3/2006 | Choate et al. | 435/262.5 |
| 7,045,063 | B2 | 5/2006 | Zhang et al. | 210/603 |
| 7,122,493 | B2 | 10/2006 | Ou et al. | |
| 7,124,817 | B2 | 10/2006 | Sunde | |
| 7,125,817 | B2 | 10/2006 | Ou et al. | |
| 7,225,085 | B2 | 5/2007 | Zhang et al. | 702/45 |
| 7,262,331 | B2 | 8/2007 | van de Beld et al. | |
| 7,316,921 | B2 | 1/2008 | Choate et al. | 435/283.1 |
| 7,419,879 | B2 | 9/2008 | Choi et al. | |
| 7,426,960 | B2 | 9/2008 | Pfeiffer et al. | |
| 7,556,094 | B1 | 7/2009 | Urynowicz | 166/246 |
| 7,556,737 | B2 | 7/2009 | Zhang | 210/603 |
| 7,640,978 | B2 | 1/2010 | Pfeiffer et al. | |
| 7,681,639 | B2 | 3/2010 | Gardes | |
| 7,696,132 | B2 | 4/2010 | Pfeiffer et al. | |
| 7,832,475 | B2 | 11/2010 | Jin et al. | |
| 7,845,403 | B2 | 12/2010 | Pfeiffer et al. | |
| 7,871,792 | B2 | 1/2011 | Pfeiffer et al. | |
| 7,909,895 | B2 | 3/2011 | Dickinson et al. | |
| 7,975,762 | B2 | 7/2011 | Pfeiffer et al. | |
| 7,977,282 | B2 | 7/2011 | Pfeiffer et al. | |

(56) References Cited

U.S. PATENT DOCUMENTS

| | | |
|---|---|---|
| 8,026,086 B2 | 9/2011 | Rywak |
| 8,051,908 B2 | 11/2011 | Pfeiffer et al. |
| 8,067,223 B2 | 11/2011 | Pfeiffer et al. |
| 8,092,559 B2 | 1/2012 | DeBruyn et al. |
| 8,105,489 B2 | 1/2012 | Jin et al. |
| 8,127,839 B2 | 3/2012 | Jin et al. |
| 8,212,087 B2 | 7/2012 | Medoff |
| 8,399,729 B2 | 3/2013 | Davis et al. |
| 8,444,725 B2 | 5/2013 | Agrawal et al. |
| 8,491,784 B2 | 7/2013 | Reynolds et al. |
| 8,637,299 B2 | 1/2014 | Heichberger |
| 8,715,980 B2 | 5/2014 | Clarke |
| 8,716,537 B2 | 5/2014 | Medoff |
| 8,759,047 B2 | 6/2014 | Datta et al. |
| 2001/0045279 A1 | 11/2001 | Converse et al. ............ 166/246 |
| 2002/0017629 A1 | 2/2002 | Mosier et al. |
| 2002/0102673 A1* | 8/2002 | Zhang et al. ................ 435/167 |
| 2004/0033557 A1 | 2/2004 | Scott et al. .................. 435/42 |
| 2004/0038354 A1 | 2/2004 | Dew et al. |
| 2004/0110645 A1 | 6/2004 | Campbell |
| 2004/0200618 A1 | 10/2004 | Piekenbrock |
| 2004/0203134 A1 | 10/2004 | Pyntikov et al. |
| 2005/0061001 A1 | 3/2005 | Maston |
| 2005/0082058 A1 | 4/2005 | Bustin et al. |
| 2005/0118130 A1 | 6/2005 | Utz et al. |
| 2006/0131074 A1 | 6/2006 | Calhoun et al. ............. 175/50 |
| 2006/0223153 A1 | 10/2006 | Pfeiffer et al. |
| 2006/0223154 A1 | 10/2006 | Kohr et al. .................. 435/166 |
| 2006/0223159 A1 | 10/2006 | Pfeiffer et al. ............. 435/252.1 |
| 2006/0223160 A1 | 10/2006 | Vanzin ........................ 435/252.4 |
| 2006/0254765 A1 | 11/2006 | Pfeiffer et al. |
| 2007/0048848 A1 | 3/2007 | Sears |
| 2007/0078665 A1 | 4/2007 | Dodson et al. ............... 705/1 |
| 2007/0158264 A1 | 7/2007 | Zhang ........................ 210/603 |
| 2007/0161077 A1 | 7/2007 | Pfeiffer et al. .............. 435/41 |
| 2007/0191303 A1 | 8/2007 | Dillon et al. ................. 514/54 |
| 2007/0243235 A1 | 10/2007 | David et al. |
| 2007/0244227 A1 | 10/2007 | Eipper et al. |
| 2007/0248531 A1 | 10/2007 | Debryun et al. |
| 2007/0251146 A1 | 11/2007 | Larter et al. ................. 48/127.5 |
| 2007/0261843 A1 | 11/2007 | Pfeiffer et al. ............... 166/246 |
| 2007/0295505 A1 | 12/2007 | Pfeiffer et al. ............... 166/263 |
| 2008/0051599 A1 | 2/2008 | Adami et al. |
| 2008/0274022 A1 | 11/2008 | Boykin et al. |
| 2009/0017513 A1 | 1/2009 | Bell et al. |
| 2009/0023612 A1 | 1/2009 | Pfeiffer et al. |
| 2009/0193712 A1* | 8/2009 | Verkade et al. ............. 44/620 |
| 2009/0246849 A1* | 10/2009 | Jin et al. ..................... 435/167 |
| 2010/0000732 A1 | 1/2010 | Downey ...................... 166/268 |
| 2010/0032157 A1 | 2/2010 | Downey ...................... 166/275 |
| 2010/0035309 A1 | 2/2010 | Havemen et al. |
| 2010/0068772 A1 | 3/2010 | Downey ...................... 435/134 |
| 2010/0081184 A1 | 4/2010 | Downey et al. .............. 435/167 |
| 2010/0139913 A1 | 6/2010 | Downey ...................... 166/246 |
| 2010/0279361 A1 | 11/2010 | South et al. |
| 2010/0330633 A1 | 12/2010 | Walther et al. |
| 2011/0027849 A1 | 2/2011 | Jin et al. |
| 2011/0087000 A1 | 4/2011 | Peters et al. |
| 2011/0151533 A1 | 6/2011 | Downey et al. |
| 2011/0262987 A1 | 10/2011 | Downey |
| 2011/0314726 A1 | 12/2011 | Jameel et al. |
| 2012/0003705 A1 | 1/2012 | Jin et al. |
| 2012/0043084 A1 | 2/2012 | Jin et al. |
| 2012/0240452 A1 | 9/2012 | Erdoes, Jr. et al. |
| 2012/0264671 A1* | 10/2012 | Carbonell et al. ........... 510/405 |
| 2013/0056393 A1 | 3/2013 | Subramani et al. |
| 2013/0149767 A1 | 6/2013 | Marion et al. |
| 2014/0199740 A1 | 7/2014 | Merrill et al. |
| 2014/0200318 A1 | 7/2014 | Shea et al. |
| 2014/0227751 A1 | 8/2014 | Datta et al. |
| 2014/0235838 A1 | 8/2014 | Stahl et al. |

FOREIGN PATENT DOCUMENTS

| | | |
|---|---|---|
| JP | S58108290 A | 6/1983 |
| JP | 09000803 A | 1/1997 |
| WO | WO7900201 A1 | 4/1979 |
| WO | WO 87/06254 | 10/1987 |
| WO | WO9425730 A1 | 11/1994 |
| WO | WO0168904 A1 | 9/2001 |
| WO | WO2004003506 A2 | 1/2004 |
| WO | WO 2005/113784 | 12/2005 |
| WO | WO 2005/115648 | 12/2005 |
| WO | WO 2006/111124 | 10/2006 |
| WO | WO 2006/118569 | 11/2006 |
| WO | WO 2006/118570 | 11/2006 |
| WO | WO 2007/022122 | 2/2007 |
| WO | WO2007022122 A2 | 2/2007 |
| WO | WO 2009/075941 | 6/2009 |
| WO | WO 2009/148569 | 12/2009 |
| WO | WO 2010/002460 | 1/2010 |
| WO | WO 2010/016957 | 2/2010 |
| WO | WO 2010/027455 | 3/2010 |
| WO | WO 2010/036756 | 4/2010 |
| WO | WO 2010105169 A1 * | 9/2010 |
| WO | WO 2011/071533 | 6/2011 |
| WO | WO 2011/075163 | 6/2011 |
| WO | WO 2011/133218 | 10/2011 |
| WO | WO 2011/142809 | 11/2011 |

OTHER PUBLICATIONS

Bumpus, J., Regulation of Coal Polymer Degradation by Fungi (DE-FG22-94PC94209), Nov. 30, 1998.
Catcheside, et al., Biological processing of coal, Appl Microbiol Biotechnol (1999) 53: 16-24, © Springer-Verlag.
Chisti, Biotechnology Advances, vol. 25, pp. 294-306 (2007).
Demain, et al., Cellulase, Clostridia, and Ethanol, Microbiology and Molecular Biology Reviews Mar. 2005 p. 124-154.
Gray, I., Reservoir Engineering in Coal Seams: Part 1—The Physical Process of Gas Storage and Movement in Coal Seams, Society of Petroleum Engineers 1986.
Green et al., International J. Coal Geology, vol. 76, pp. 34-45 (2008).
Hargreaves, S., Exxon profit soars, but misses forecasts, CNNMoney.com, May 1, 2008.
Isbister et al., Chapter 7, Biogasification of Low Rank Coal, Microbial Transformations of Low Rank Coals pp. 139-156, © 1993 by CRC Press, Inc.
Jain, et al., Anaerobic bioprocessing of Wyodak (USA) coal, Fuel, vol. 70, pp. 573-576 (1991).
Kalscheuer, et al., Microdiesel: *Escherichia coli* engineered for fuel production, Microbiology (2006) 152, p. 2529-2536.
Kim et al., Composition of corn dry-grind ethanol by-products: DDGS, wet cake, and thin stillage, Bioresource Technology 99 (2008) 5165-5176.
Klasson, et al., Direct Bacterial Conversion of Coal to Liquid Fuels, Microbial Transformations of Low Rank Coal, in Crawford, D.L. (Ed.) Microbial Transformations of Low Rank Coals, CRC Press, Boca Raton, Chapter 5, p. 93-110 (1993).
Larsen, et al., Solvent Extraction of Coals during Analytical Solvent Swelling, A Potential Source of Error, Energy & Fuels 1991, 5, 57-59, © 1991 American Chemical Society.
Scott, A., Improving Coal Gas Recovery with Microbially Enhanced Coalbed Methane, Coalbed Methane: Scientific Environmental and Economic Evaluation, Mastaletze, M., Glikson, M., and Golding, S. Editors 1999.
Scott, A., Limitations and Benefits of Microbially Enhanced Coalbed Methane, INTERGAS '95, May 15-19, 1995, the University of Alabama, Tuscaloosa, Alabama p. 423-431.
Shaw et al., The Role of Initial Reaction Conditions in Direct Coal Liquefaction, Ind. Eng. Chem. Res. 1989, 28, 1795-1801.
Shui, et al., Effect of hydrothermal treatment on the extraction of coal in the $CS_2$/NMP mixed solvent, Fuel 85 (2006) p. 1798-1802.
Somerton et al., Effect of Stress on Permeability of Coal, Int. J. Rock Mech. Min. Sci & Geomech., vol. 12, pp. 129-145 (1975).
Spolaore et al., J. Bioscience & Bioengineering, vol. 101, pp. 87-96 (2006).

(56) References Cited

OTHER PUBLICATIONS

Toerien, et al., Anaerobic Digestion, 1. The Microbiology of Anaerobic Digestion, Water Research, vol. 3, pp. 385-416, Pergamon Press (1969).

Walsh, J.B., Effect of pore pressure and confining pressure on fracture permeability, International Journal of Rock Mechanics and Mining Sciences & Geomechanics Abstracts vol. 18, Issue 5, Oct. 1981, pp. 429-435.

Yoshii et al., Unusual effects of catechol upon the hydroliquefaction of coal, Letters to the Editor, Fuel 1982 vol. 61, Sep. 1982, pp. 865-866.

Zhang et al., Toward an Aggregated Understanding of Enzymatic Hydrolysis of Cellulose: Non-complexed Cellulase Systems, Biotechnology and Bioengineering, vol. 88, No. 7, Dec. 30, 2004.

Zhu, et al., Dissolution of cellulose with ionic liquids and its application: a mini-review, Green Chemistry, 2006, vol. 8, pp. 325-327.

International Search Report and Written Opinion for PCT/US10/03131, mailed Feb. 8, 2011.

International Search Report and Written Opinion for PCT/US10/03133, mailed Feb. 10, 2011.

International Search Report and Written Opinion for PCT/US11/00712, mailed Jul. 5, 2011.

International Search Report and Written Opinion for PCT/US2011/00819 mailed Aug. 12, 2011.

International Search Report and Written Opinion for PCT/US09/03341, mailed Jul. 23, 2009.

International Search Report and Written Opinion for PCT/US09/03917, mailed Aug. 13, 2009.

International Search Report and Written Opinion for PCT/US09/04572, mailed Oct. 5, 2009.

International Search Report and Written Opinion for PCT/US09/04945, mailed Oct. 22, 2009.

Fukuda et al., J. Biosci. Bioeng., Vo. 92, pp. 405-416 (2001).

Pan et al., JAOCS, vol. 78, pp. 553-554 (2001).

Aminian, K., Coalbed Methane—Fundamental Concepts, Petroleum & Natural Gas Engineering Department, West Virginia University, (2003).

Barik et al., Biological Production of Ethanol from Coal Synthesis Gas, in Bioprocessing and Biotreatment of Coal, Marcel Dekker, 1$^{st}$ Ed., Chapter 8, pp. 131-154 (1990).

Jones et al., Int'l J. Coal Geology, vol. 76, pp. 138-150 (2008).

EPO Supplemental Search Report for Co-Pending Appl'n EP 10838018—Nov. 5, 2013.

Strapoc et al., Applied and Environmental Microbiology, vol. 74, pp. 2424-2432 (2008).

Wang, Y., et al., "Anaerobic Biodegradability of Cellulose and Hemicellulose in Excavated Refuse Samples Using a Biochemical Methane Potential Assay," Journal of Industrial Microbiology, 1994, vol. 13, pp. 147-153.

P039192M Statement of Grounds and Particulars by Opponent Nov. 3, 2014, 26 pages.

Eden, C., "Combined Landfill Gas and Leachate Extraction Systems," QED Environmental Systems, Inc., Retrieved from www.environmental-expert, 2004, 14 pages.

The Asian Biomass Handbook: a guide to Biomass Production and Utilization, The Japan Institute of Energy (JIE), Tokyo, 2008, pp. title page-326.

Biological Gasification of Coals Final Report Work Performed Under Contract No. DE-AC21-87MC23285; U.S. Department of Engergy; Office of Fossil Energy; ArcTech, Inc.; 2009; pp. 1-130.

Toerien, D. F., et al., "Anaerobic Digestion I. The Microbiology of Anaerobic Digestion," Water Research, 2009; vol. 3, pp. 385-416.

Isbister, J. D., et al., "Microbial Transformations of Low Rank Coals: Chapter 7," Biogasification of Low Rank Coals; 1967; pp. 139-156.

Notice of Reasons for the Rejection; Mailed Mar. 3, 2015 for the corresponding JP Application No. JP2012-544476.

Davison, B.H., et al., "Utilization of Microbially Solubilized Coal," Preliminary Studies on Anaerobic Conversion, Scientific Note, Applied Biochemistry and Biotechnology, 1990, vol. 24/25, pp. 447-456.

Japanese Office Action; Mailed May 12, 2015 for corresponding JP Application No. JP2013-506136 along with a machine generated English Translation.

\* cited by examiner

US 9,102,953 B2

BIOGASIFICATION OF COAL TO METHANE AND OTHER USEFUL PRODUCTS

This application claims priority of U.S. Provisional Application 61/329,862, filed 30 Apr. 2010, and U.S. Provisional Application 61/284,483, filed 18 Dec. 2009, the disclosures of which are incorporated herein by reference in their entirety.

FIELD OF THE INVENTION

The present invention provides methods for the generation and production of methane, carbon dioxide, gaseous and liquid hydrocarbons and other valuable products from coal, using coal separation, solubilization, pretreatment and conversion via efficient, high-rate anaerobic fermentation.

BACKGROUND OF THE INVENTION

Anaerobic digestion is a well-known process used to obtain usable methane gas and other useful products from manure, waste sludge and other predominantly organic materials. Organic materials provide the substrate for anaerobic fermentation or biodegradation, and may be comprised of a wide range of organic carbon sources, such as plants and crop wastes, sewage sludge, and other refuse. Anaerobic digestion is a fermentation or biodegradation process that breaks down or degrades these carbonaceous materials to produce gases, such as methane and carbon dioxide. Anaerobic digestion utilizes consortia of microorganisms to degrade and then convert the carbonaceous material to produce gases, under certain pressure, temperature and other environmental conditions.

The United States has over 1000 Billion tons of coal resources, and more than half of this resource is low-rank coal. Coal is a heterogeneous material that consists of carbon, hydrogen, oxygen, nitrogen, sulfur and other minerals. The combustion of coal releases oxides of carbon, nitrogen and sulfur, as well as some heavy metals such as mercury, into the atmosphere. Coal combustion generates the most pollution of any fossil fuel resource. Low-rank coals have low market value commensurate with their Btu content, and also generate a large amount of pollutants, making their use increasingly unattractive for power generation.

A number of different coal conversion technologies that employ thermal and/or chemical processes have been in commercial use for many years but these processes convert coal to gases and chemicals under high pressures and temperatures with high capital and operating costs, relatively low thermodynamic efficiency, and generation of significant amounts of carbon dioxide and other gaseous emissions, and also require large amounts of water in the process with solid waste streams that must be disposed of safely.

The present invention solves these problems by a process of bioconversion of coal to much cleaner-burning methane and other useful products to increase the supply of these energy resources, to effectively utilize a fossil fuel resource that may otherwise be wasted or not used, and to employ technology that has a low environmental impact with high efficiency. Consequently, anaerobic bioconversion of coal has lower capital and operating costs, has higher thermodynamic efficiencies, and produces much less gaseous emissions and solid wastes.

BRIEF SUMMARY OF THE INVENTION

In one aspect, the present invention relates to a process for converting coal ex situ into methane and other useful products, comprising:

(a) treating coal with a liquid that solubilizes at least a portion of the coal, (b) treating at least a portion of the product of step (a) with a hydrolytic microbial organism to produce a product containing fatty acids, (c) treating at least a liquid portion of the product from step (b) with an anaerobic microbial population that generates methane to produce a product containing methane thereby converting coal ex situ.

In preferred embodiments, steps (a), (b) and (c) of the above process are performed separately, e.g., in different vessels.

In another embodiment, the coal used in step (a) is pulverized coal, preferably coal that has been treated to remove at least a portion of non-coal impurities.

In one embodiment, step (a) of the above process comprises:

(i) treating coal with an alkali, such as sodium hydroxide or potassium hydroxide, (ii) treating at least a portion of the product from (i) with an organic acid (e.g., a carboxylic acid) of up to 4 carbon atoms or a benzoic acid, or a salt or ester of any of these acids, to solubilize at least a portion of the coal, and (iii) treating at least a portion of the product from (ii) with hydrogen peroxide in the presence of iron.

In a preferred embodiment, the liquid in step (a), preferably in (ii), contains acetic acid and/or a salt or ester of acetic acid or contains benzoic acid and/or a salt or ester of benzoic acid.

In one embodiment of the aforementioned process, the product from step (a) treated in step (b) is a liquid portion obtained from (iii). In another embodiment thereof, the hydrolytic organism of step (b) includes an acetogen.

In another embodiment, the liquid of step (a) is a solvent selected from aromatic hydrocarbons, preferably phenanthrene, chrysene, fluoranthene and pyrene, nitrogenous ring aromatics (preferably acridine or carbazole), anthracene, fluorine, catechol (or pyrocatechol), creosote and heavy oils.

a fluids processor is represented as a polygon (19); and a recirculation flow line is represented by the dotted line numbered (20).

Figure 3:
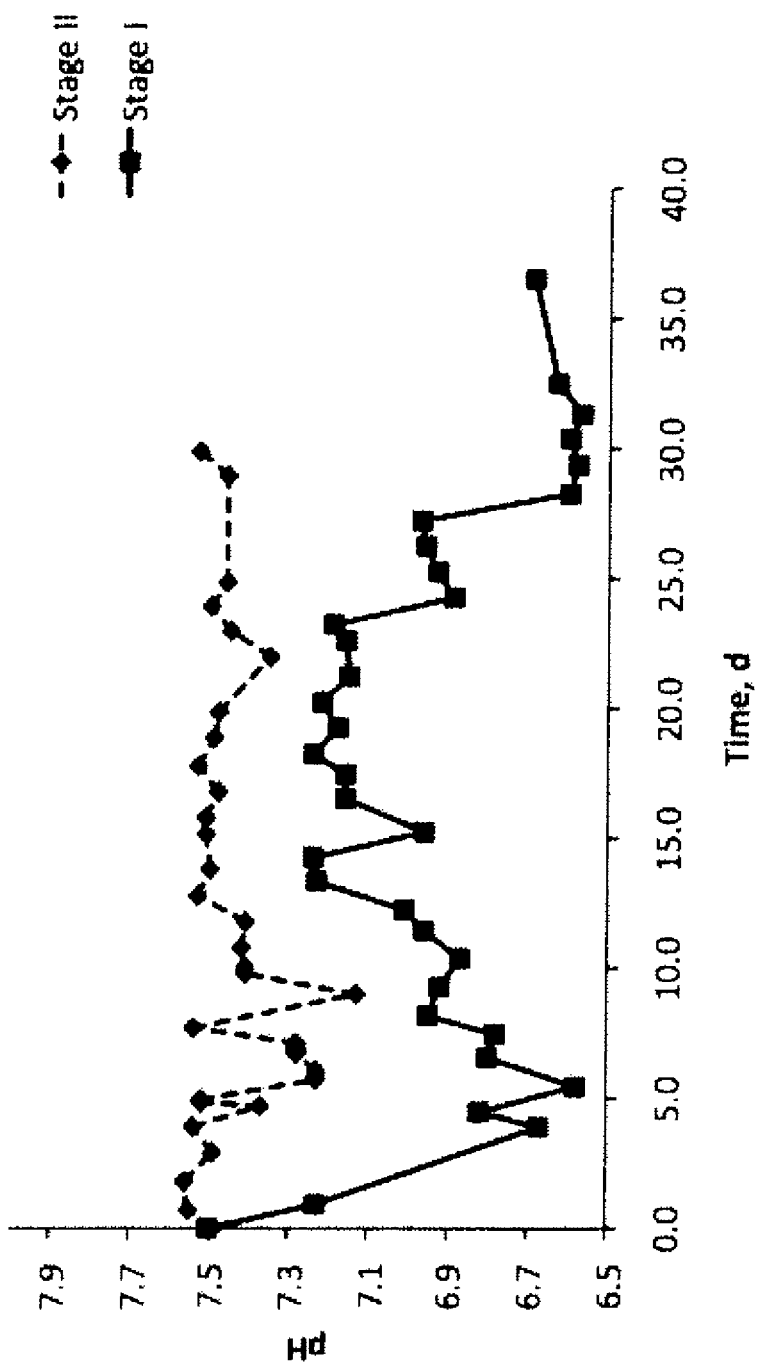

FIG. 3 shows the pH of the reactors during the bioconversion of coal as a plot of the pH of the hydrolysis vessel and the biogasification reactor of the example, measured daily.

Figure 4:
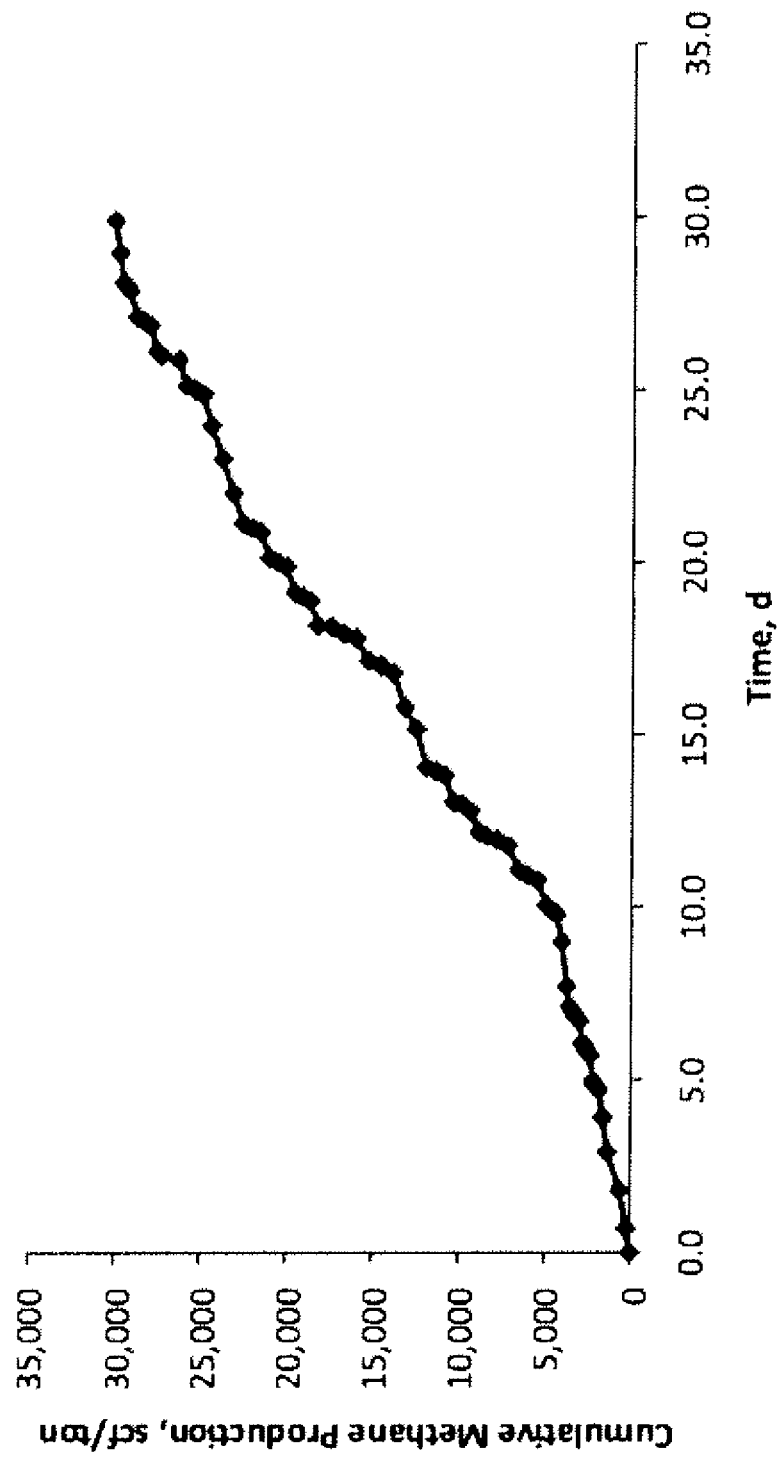

FIG. 4 is a plot of cumulative methane production in the system showing cumulative biogas and methane production rates from the biogasification reactor of the example.

Figure 5:
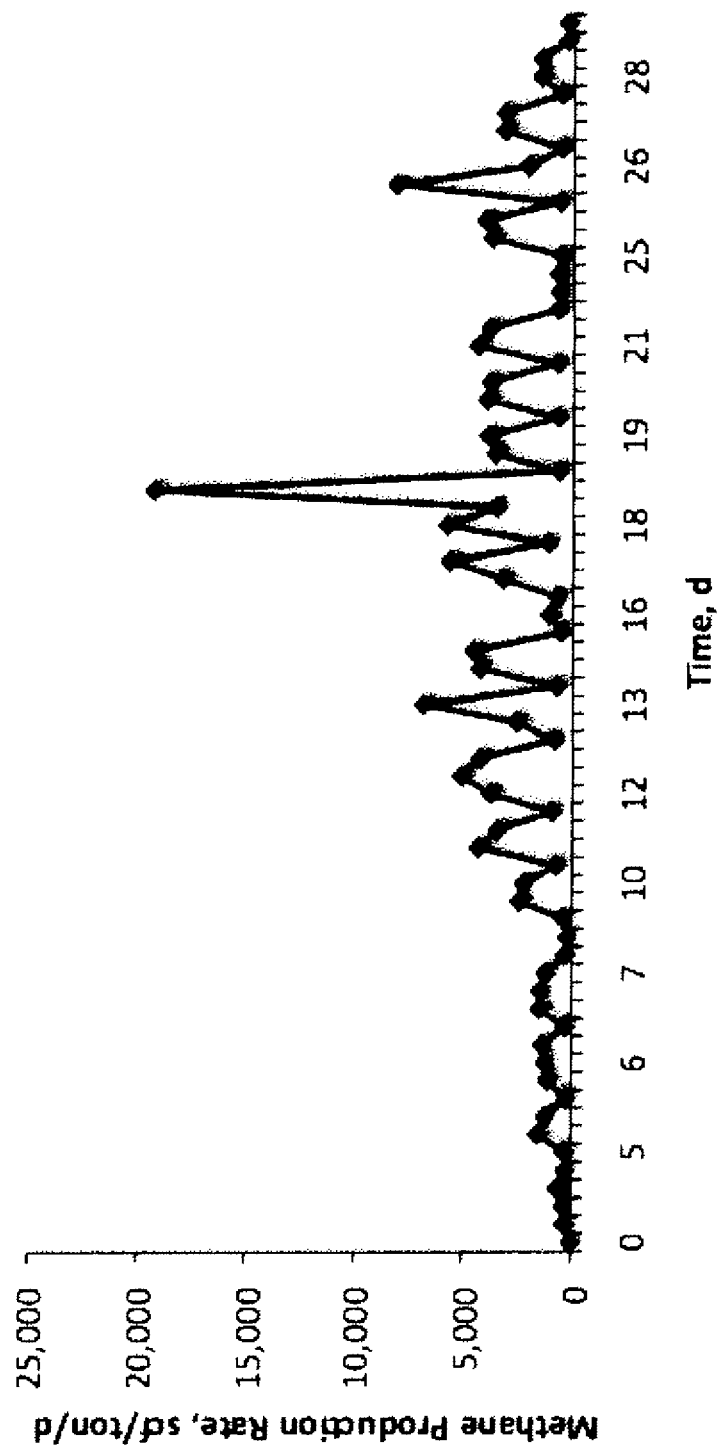

FIG. 5 is a plot of daily biogas and methane production from the biogasification reactor of the example.

Figure 6:
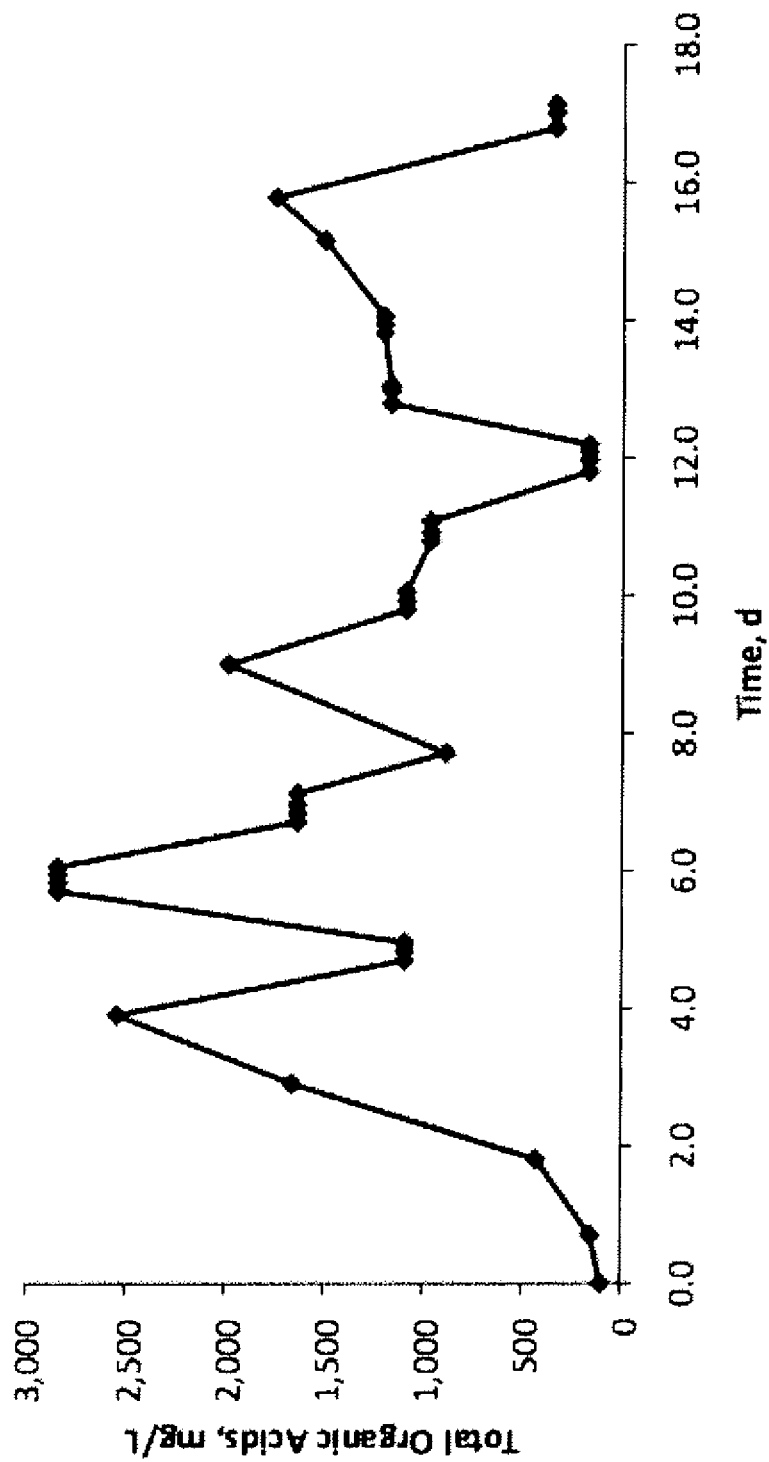

FIG. 6 is a plot of percent of total organic acid present in the hydrolysis reactor of the COMCAPS system.

Figure 7:
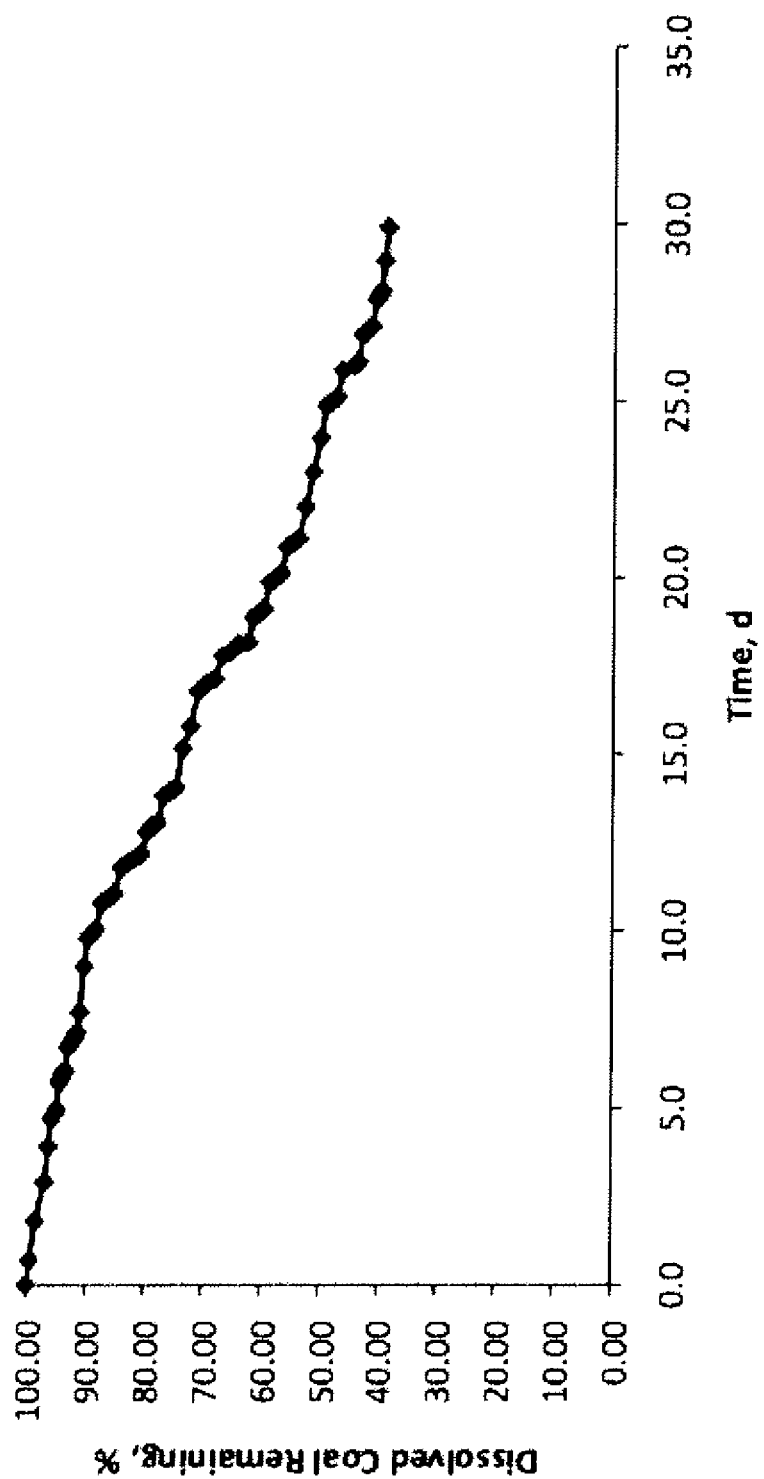

FIG. 7 is a plot of percent of remaining dissolved coal carbon in the hydrolysis reactor of the COMCAPS system.

DEFINITIONS

As used herein, the phrase "converting coal" refers to the chemical and/or physical conversion of coal into methane and other products useful in energy generation. As used herein, the term "bioconversion" refers to the conversion of carbonaceous molecules (such as those in a carbon-bearing formation, for example, coal, into methane and other useful gases and liquid products, preferably by indigenous or non-indigenous microbes, or such conversion of coal that has been removed from such a formation prior to treatment. Such bioconversion may be stimulated to occur by the application of electricity from a chemical or physical source.

As used herein, the term "solubilizing" or "solubilized" when used with reference to "coal" means that after treatment with the salt or ester of acetic acid, the solid content of the coal has been reduced. Without limiting the foregoing and/or limiting the invention, it is believed that such reduction in solid content is achieved by (i) the breaking of bonds in the coal matrix resulting in chemical breakdown of portions of the coal and/or (ii) cleaving of bonds holding carbon layers together. Thus, the solubilization of the coal may involve one or more of a chemical break-down of the coal and/or cleaving of bonds.

As used herein, the term "coal" refers to a natural dark brown to black carbon-bearing graphite-like material used as a fuel, formed from fossilized plants and consisting of amorphous carbon with various organic and some inorganic compounds.

The terms "biogasification" and "methanogenesis" are used herein essentially interchangeably.

As used herein, the term "acetate" refers to the salt that one or more of the hydrogen atoms of acetic acid are replaced by one or more cations of the base, resulting in a compound containing the negative organic ion of $CH_3COO-$. In accordance with the invention, said salts or esters of acetic acid may or may not be mixed with water. In one preferred embodiment, the salts or esters of acetic acid are used in admixture with water. It is to be appreciated that when such acetate salts are employed using a water solvent, some acetic acid may or will be formed (depending on the final pH) and will participate in the solubilization process. For purposes of the invention, a similar definition is to be understood where a salt of any other carboxylic acid, such as benzoic acid, is used for like purposes.

As used herein, the term "aromatic alcohol" means an organic compound having the formula ROH, wherein R is a substituted or unsubstituted aromatic group, which the aromatic group may be a monocyclic ring or a fused ring. In one embodiment, the aromatic group R is unsubstituted. In another embodiment, —OH R is substituted with one or more of a hydrocarbon group and/or an —OH group(s). In some embodiments, the —OH is present on the aromatic ring, or is present in a substituent of said ring or both.

As used herein, the term "cycloaliphatic alcohol" means an organic compound having the formula $R_1OH$, wherein $R_1$ includes a substituted or unsubstituted cycloaliphatic group. In one embodiment, the substituent group may be one or more of —OH and or an aliphatic hydrocarbon. Preferred cycloaliphatic alcohols include, but are not limited to, cyclopropanols, cyclobutanols, cyclopentanols, cyclohexanols, and cycloheptanols.

As used herein, the phrase "microbial consortium" refers to a microbial culture (or natural assemblage) containing 2 or more species or strains of microbes, especially one in which each species or strain benefits from interaction with the other(s).

As used herein, the following abbreviations have the indicated meaning: VS, volatile solids; SRT, solid retention time; HRT, hydraulic retention time; VFA, volatile fatty acid; AE, acid ester.

DETAILED DESCRIPTION OF THE INVENTION

In one aspect, the present invention relates to a method of bioconversion of coal to methane, carbon dioxide, and other valuable gaseous and liquid products in a multi-step process that may include particle size reduction, separation of non-coal materials, addition of chemicals, and multi-stage anaerobic fermentation.

The present invention provides methods for converting coal ex situ, comprising:

(a) treating coal with a liquid, preferably acetic acid and/or a salt or ester of acetic acid, that solubilizes at least a portion of the coal, (b) treating at least a portion of the product of step (a) with a hydrolytic microbial population to produce a product containing fatty acids, (c) treating at least a liquid portion of the product from step (b) with an anaerobic microbial population that generates methane to produce a product containing methane thereby converting coal ex situ.

In one embodiment, step (a) of the above process comprises:

(i) treating coal with an alkali, such as sodium hydroxide or potassium hydroxide, (ii) treating at least a portion of the product from (i) with an organic acid (e.g., a carboxylic acid) of up to 4 carbon atoms or a benzoic acid, or a salt or ester of any of these acids, to solubilize at least a portion of the coal, and (iii) treating at least a portion of the product from (ii) with hydrogen peroxide in the presence of iron.

While the above order of steps is a preferred embodiment, in other embodiments the coal may be treated with the solvents of (i), (ii) or (iii) in any order or combination to facilitate coal solubilization and a specific order is not necessitated by the methods of the invention. In addition, such solvents may be used separately or in any combination to achieve solubilization of coal, some of which solvents may not be required at all.

In one example of the method(s) of the invention, the liquid of step (a) is a solvent selected from aromatic hydrocarbons, creosote and heavy oils. In preferred embodiments thereof, the solvent is an aromatic hydrocarbon, preferably one or more of phenanthrene, chrysene, fluoranthene and pyrene, nitrogenous ring aromatics, anthracene, fluorine, and catechol. Such nitrogenous ring aromatic is preferably acridine or carbazole.

In another example, the liquid of step (a) is selected from an alkali, a carboxylic acid, a salt of a carboxylic acid, an ester of a carboxylic acid, and a peroxide. When said liquid is an alkali, it is preferably one or more of NaOH, KOH or a Lewis base. In one example, the liquid is a C1-C4 carboxylic acid, carboxylic acid is acetic acid, a salt of a C1-C4 carboxylic acid or an ester of a C1-C4 carboxylic acid. In one embodiment, said liquid is acetic acid or a salt or ester of acetic acid, or is benzoic acid, or a salt or ester of benzoic acid. When said liquid is a peroxide, it is preferably hydrogen peroxide, for example, hydrogen peroxide in the presence of iron.

In a non-limiting embodiment, the treating is effected at temperatures in the range 0 to 300° C., preferably temperatures of 0 up to 200° C., more preferably at a temperature of 10 to 200° C.

In a non-limiting embodiment, the treating is effected at a pH in the range 2 to 12, preferably 3 to 11, more preferably 5 to 10, and the like, or may lie solely in the acid or alkaline range, such as 1 to 6, 2 to 5, or 3 to 4, or in the range 8 to 13, or 9 to 12, or 10 to 11.

In a non-limiting embodiment, the treating is effected at selected pressures, including, in specific processes, atmospheric pressure, above atmospheric pressure or below atmospheric pressure. For example, in treating coal deposits in situ, such as in a well, the pressure is the pressure prevailing in the deposit or is an elevated pressure determined by controlling the pressure at which liquid is introduced into the well.

In specific examples of the methods of the invention, the liquid used in step (a) is one or more of acetic acid, a salt of acetic acid (i.e., an acetate) or an ester of acetic acid.

Preferred salts or esters of acetic acid include, but are not limited to, methyl acetate, ethyl acetate, propyl acetate, isopropyl acetate, n-butyl acetate, isobutyl acetate, amyl acetate, isoamyl acetate, hexyl acetate, heptyl acetate, octyl acetate, nonanyl acetate, decyl acetate, undecyl acetate, lauryl acetate, tridecyl acetate, myristyl acetate, pentadecyl acetate, cetyl acetate, heptadecyl acetate, stearyl acetate, behenyl acetate, hexacosyl acetate, triacontyl acetate, benzyl acetate, bornyl acetate, isobornyl acetate and cyclohexyl acetate.

A like range of salts or esters may be used in the methods of the invention where the acid is benzoic acid, or any other carboxylic acid, instead of acetic acid, so that the same range of substituents of salts and/or benzoates could be utilized as recited above for acetates.

In one embodiment, the liquid of step (a) is a solvent, or solvents, useful in facilitating the process of the invention, such as aromatic hydrocarbons, creosote and/or heavy oils. The preferred aromatic hydrocarbons include phenanthrene, chrysene, fluoranthene and pyrene, Nitrogenous ring aromatics, for example, acridine and carbazole, as well as catechol (or pyrocatechol), are also suitable as solvents in the processes of the invention. Aromatics such as anthracene and fluorene may also be used A useful solvent includes any of the foregoing, as well as mixtures, preferably a eutectic composition, thereof. Such mixtures can usefully be dissolved in a carrier liquid, for example, a heavy oil (such a mixture being no more than about 5% to 10% of the dissolved solvent). Such solvents are most useful when heated to temperatures in the range of 80 to 400° C., preferably 80 to 300° C., more preferably 100 to 250° C., and most preferably at least about 150° C. Temperatures higher than about 400° C. are less advantageous.

In one embodiment, the liquid of step (a) is a solvent, or solvents, includes a phosphite ester. An ester of phosphite is a type of chemical compound with the general structure $P(OR)_3$. Phosphite esters can be considered as esters of phosphorous acid, $H_3PO_3$. A simple phosphite ester is trimethylphosphite, $P(OCH_3)_3$. Phosphate esters can be considered as esters of phosphoric acid. Since orthophosphoric acid has three —OH groups, it can esterify with one, two, or three alcohol molecules to form a mono-, di-, or triester. Without being bound by any particular mechanism, it is likely that the chemical compounds including esters of phosphite and phosphate, or an oxoacid ester of phosphorus, or a thioacid ester of phosphorus; or a mixture of an oxoacid of phosphorus and an alcohol, or a mixture of an thioacid of phosphorus and an alcohol, or a mixture of a thioacid of phosphorus and an alcohol and acetic acid and/or a salt or ester of acetic acid, react with carbon-bearing molecules to break carbon bonds within the molecules and add hydrogen molecules to these carbon-bearing molecules, to thereby yield a range of smaller carbon-bearing molecules, such as carbon monoxide, carbon dioxide and volatile fatty acids, which are in turn more amenable to bioconversion by methanogenic microbial consortia to methane and other useful hydrocarbons. In one non-limiting example, the reaction products produced from reaction of coal with the introduced oxoacid ester of phosphorus or the thioacid ester of phosphorus, or the mixture of an oxoacid of phosphorus and an alcohol, or the mixture of a thioacid of phosphorus and an alcohol, stimulates a methanogenic microbiological consortium in the subterranean formation to start producing, or increase production of, methane and other useful products.

The methods of the invention are conveniently carried out ex situ (where carbonaceous material, such as coal, is first removed from a formation and then treated according to the methods of the invention), or by methods described in U.S. Pat. No. 3,990,513, which is hereby incorporated by reference, each incorporating a method of the invention.

The present invention affords numerous advantages over the art. For example, the inventive process converts coat into hydrogen, methane, carbon dioxide and other valuable products that can be utilized as a clean fuel for heating, power generation and transportation. The system utilizes pre-processing steps including particle size reduction and solubilization pre-treatment to enhance and accelerate bioconversion. A buffer tank is also utilized to equilibrate physical and chemical properties of the volatile fatty acids and acid esters produced in step (b), such as pH, temperature, conductivity, nutrients and biochemical oxygen demand, collected from different hydrolysis reactors and provide a method to control the volatile fatty acid and ester loading rate into the biogasification reactor. This equilibration process provides for greater and more consistent gas yields, such as a much greater concentration of methane and reduced concentration of carbon dioxide, because the bacteria in the biogasification reactor are able to more efficiently process a consistent flow of volatile fatty acids and esters into the reactor. The system is also designed to maximize and optimize the use of the hydrolysis reactor volume in order to achieve very high conversion efficiency of the coal, in terms of maximum gas production rates at lower capital and operating costs. The process enables hydrogen gas produced in the hydrolysis reactor and the buffer tank to be used in the biogasification reactor, and at a stable, high rate, yielding higher conversion rates to methane.

The present invention also contemplates the bioconversion of carbon-bearing materials in subterranean formations to methane and other useful hydrocarbons by treating the subterranean formation with a solution containing at least one of an oxoacid ester of phosphorus or a thioacid ester of phosphorus; one or more cyclic and/or aromatic alcohols; and one or more other chemical compounds or chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts.

Such embodiments include the introduction of certain chemical compounds including one or more aromatic alcohols and/or cyclic aliphatic alcohols or mixtures of aromatic and/or cyclic alcohols, and mixtures of one or more aromatic alcohols and/or cyclic aliphatic alcohols, hydroxides, peroxides and iron, that can rapidly and efficiently break down or solubilize large carbonaceous molecules into smaller compounds that may in turn be more readily bioconverted into methane and other useful hydrocarbon products, into a carbon-bearing subterranean formation, at rates such that the solubilization products may be metabolized by methanogenic consortia and converted to methane and other useful hydrocarbons.

In accordance with one embodiment of the invention, coal is treated to solubilize at least a portion of the coal as hereinabove described as part of the process for bioconverting the coal to a product that includes methane and/or other useful products. In such a process, the bioconversion is effected in conjunction with such treating or at least a portion of product from such treating may then be subjected to bioconversion to produce a product that includes methane.

The coal solubilization system of the present invention preferably incorporates coal comminution to produce coal particles in a specified size range, a coal impurities separation unit, chemicals treatment tanks, at least one hydrolysis reactor, a buffer tank, and a biogasification reactor. In the system, coal is comminuted or ground to a specified particle size range that enables high surface area for solubilization pretreatment, and gravity separation from non-coal particles. The ground coal particles are transferred to a coal separation unit, where the non-coal particles are removed by specific gravity differentiation. The coal particles are then transferred to solubilization treatment tanks, where chemicals are added that solubilize the coal to a predominantly liquid form, having a composition of mostly smaller size hydrocarbon molecules. The solubilized coal is then transferred into the hydrolysis reactor, where it is bioconverted into volatile fatty acids and esters of acids. The soluble volatile fatty acids and acid esters, such as acetate produced in the hydrolysis reactor are transferred preferably to a buffer tank wherein they are optionally equilibrated with respect to physical and chemical properties. The equilibrated volatile fatty acids and esters are then transferred to the biogasification reactor at a controlled rate in order to optimize growth rate of the methanogenic bacteria and the production of methane gas.

The present invention provides a method for producing, for example, methane, hydrogen and carbon dioxide and combinations thereof by a multi-step preprocessing phase and two-phase anaerobic digestion phase process. In a preferred embodiment, the method includes (a) grinding or shearing the raw coal into particles of a specific size range, (b) transferring the coal particles to a coal separation unit that utilizes specific gravity differences between the coal and non-coal particles to separate and remove the non-coal particles from the process, (c) transferring the coal particles to a tank or tanks where they are solubilized by chemicals to predominantly liquid phase organic molecules, (c) transferring the solubilized coal liquids to a hydrolysis reactor, (d) incubating the first hydrolysis mixture in a first hydrolysis phase vessel for a first period of incubation, the first hydrolysis mixture comprising a microbial consortium and an aqueous liquid obtained from the coal solubilization, under anaerobic conditions, the first hydrolysis phase vessel comprising therein a hydrolytic bacterial culture for which the solubilized coal material is a substrate, (e) after the first period of incubation, transferring a portion of the aqueous liquid of the first mixture residing in the first hydrolysis phase vessel to a buffer tank, forming a buffer tank mixture, (f) transferring a portion of the buffer tank mixture to a gasification reactor comprising a methanogenic bacterial culture therein for which the volatile fatty acid and esters are a substrate, forming a biogasification mixture, (g) incubating the biogasification mixture for a second incubation period during which gas which is a member selected from methane, hydrogen and mixtures thereof is generated, and (h) transferring a portion of the biogasification mixture into the first hydrolysis phase vessel for a third incubation period.

Hydrogen, methane and carbon dioxide gases are produced in the hydrolysis reactor and the buffer tank, along with the volatile fatty acids and acid esters. These gases are circulated and re-circulated among the buffer tank and biogasification reactor. The mixtures in the hydrolysis vessels, the buffer tank and the biogasification reactor are agitated or stirred intermittently or continuously to optimize the bioconversion process. After a selected period of time, a portion of the mixture in the biogasification reactor is recirculated back to the hydrolysis phase reactor. The solid(s) effluent from the biogasification reactor is/are filtered and dewatered, with the resultant fluid recirculated back to the solubilization tank for use in solubilizing coal, and the effluent solid placed in a waste disposal facility, landfill, or utilized beneficially to enhance soil quality or for other purposes.

In a preferred embodiment, the solubilization tank, the hydrolysis reactor, the buffer tank and the biogasification reactor are connected via a series of conduits or pipes through which liquids and gases are transferred. Thus the device also comprises a first conduit connecting the solubilization tank outlet to the hydrolysis reactor inlet, a second conduit connecting the hydrolysis reactor outlet to the buffer tank inlet, a third conduit connecting the buffer tank outlet with the biogasification reactor inlet, and a fourth conduit connecting the biogasification reactor outlet with the hydrolysis reactor inlet. A fifth conduit connecting the biogasification effluent process tank to the solubilization tank may also be included in the device.

Other features, objects and advantages of the present invention and its preferred embodiments will become apparent from the detailed description that follows.

The present invention provides improved methods for the solubilization and anaerobic digestion of coal to produce hydrogen and methane gases and devices with which to perform these methods.

In one example, the present invention makes use of a COMCAPS digestor system, which is a combined mechanical process, chemical process and two phase anaerobic digestion system. This system employs a coal particle processor to reduce the coal to uniform particles of a specific size range, a coal separator system to remove and discard non-coal particles, chemical solubilization treatment tanks, at least one hydrolysis reactor, a buffer tank, a biogasification reactor, and an effluent processor. In the COMCAPS system, raw feedstock coal is communitized, pulverized or sheared to particles of a specific size range. The raw coal particles are then subjected to a specific gravity separation system, and the non-coal particles are separated out and discharged from the system. The coal particles are then transferred to chemical solubilization treatment tanks, where the coal is placed into contact with chemicals that solubilize it to a predominantly liquid form consisting of smaller organic molecules, and which may include VFA's and esters, such as acetate. The solubilized coal liquids and solids are transferred to the hydrolysis reactor, where they are converted to VFA's and acid esters, such as acetate. In a preferred embodiment, The soluble VFA's and acid esters are transferred to a buffer tank, in which the physical and chemical properties of the VFA's and acid esters are equilibrated, allowing controlled loading of the VFA's and acid esters into the biogasification reactor. This in turn results in maintenance of a stable pH, temperature and other conditions optimum for maximum methane production. The equilibrated VFA's and acid esters are then transferred to a biogasification reactor for production of gases. The remaining liquid in the biogasification reactor is then recirculated back to the hydrolysis reactor. The effluent solids from the biogasification reactor are filtered and dewatered, and the fluids are recirculated back to the solubilization treatment tank.

The present invention provides, for example, a process for methane, hydrogen and carbon dioxide production by a multi-stage system including coal solids reduction, separation, solubilization and two-phase anaerobic digestion. The process comprises coal particle size reduction, removal of non-coal particles and solubilization of the coal, followed by incubating a mixture having the solid coal, solubilized coal and an aqueous liquid component, under anaerobic conditions and containing a hydrolysis means therein. Hydrogen and carbon dioxide gases are primarily produced in the hydrolysis reactor, but methane can also be produced in this process.

In a preferred embodiment, after a first period of incubation, VFA's and AE's residing in the hydrolysis digestor are transferred through an outlet located on the side of the hydrolysis reactor to a buffer tank in which physical properties of the VFA's and AE's are equilibrated. Hydrogen and carbon dioxide gases could also be produced in the buffer tank. After the VFA's and AE's are equilibrated, the equilibrated VFA's and AE's are transferred to a methane phase digestor or biogasification reactor and a methanogenesis means therein. In the methane phase digestor, the equilibrated VFA's and AE's are combined with the methanogenesis means to form a resulting mixture. The resulting mixture is incubated for a second period of time, generating methane and carbon dioxide gases. The resulting mixture is optionally intermittently agitated and/or stirred, then allowed to remain still for a period of time. After the selected period of time, a portion of the resulting mixture residing in the methane phase digestor is recirculated back to the hydrolysis reactor. Alternatively or in addition, effluent from the methane phase digestor is filtered and dewatered and the fluids are recirculated back to the solubilization treatment tank.

The process of the invention can be practiced with any type of coal, such as lignite, sub-bituminous coal, bituminous coal, semi-anthracite coal, or anthracite coal. It may also be practiced with oil shale, a sedimentary rock containing kerogen, a fossilized mixture of insoluble organic material that when heated breaks down into petroleum and natural gas. Kerogen consists of carbon, hydrogen, oxygen, nitrogen and sulfur, and forms from compacted organic material, including algae, pollen, spores and spore coats, and insects. The process of the invention may also be practiced with any mixture of coal and/or oil shale and/or other carbonaceous organic substrate including but not limited to sewage sludge, food waste, forestry waste and agricultural waste.

In one embodiment, the feedstock coal is ground, pulverized or otherwise reduced in particle size to a range of sizes to yield a high surface area to mass ratio. In a preferred embodiment, the particle size range is between 100 to 250 microns in diameter.

Impurities in the ground or pulverized feedstock coal are removed by separation, due to differences in the specific gravity of the coal and the non-coal impurities, using any of several types of separation techniques, such as float-sink or centrifugation.

The ground or pulverized and feedstock coal with reduced levels of impurities can be treated with solubilization chemicals to reduce the molecular weight of the coal constituents, depolymerize the constituents, and change the chemical composition of the constituents to chemicals and compounds that are more amenable to hydrolysis. Useful chemicals for solubilization include, but are not limited to, acetic acid and/or salts and esters of acetic acid, aryl alcohols, sodium hydroxide, potassium hydroxide, benzoic acid, benzoate, C1-C4 carboxylic acids, hydrogen peroxide, Lewis bases, metal ions and phosphite esters, in any of a range of combinations, as well as any other solvents recited herein.

In a preferred embodiment, the solubilization chemicals are combined with water and the feedstock coal and stirred for a period of at least 48 hours, at a temperature of about 40° C., in several sequential steps with specific chemicals added to the solution at each step. Coal solids that remain unsolubilized following a series of solubilization treatment steps is recirculated through the pretreatment process to yield optimum solubilization.

The hydrolysis phase, the buffer tank and the methanogenesis phase are operative over variable pH ranges that are related to the nature of the solubilized coal, VFA and AE substrate and the amount of total solids in the solubilized coal, VFA and AE substrate. In a preferred embodiment, the pH of the hydrolysis reactor is maintained from about 5.5 to 6.5, and the biogasification phase pH is maintained from about 7.0 to about 7.5.

The entire system is operated at a constant or variable temperature between 10° C. to about 70° C., more preferably between about 35° C. to about 65° C., and most preferably between about 40° C. to about 60° C.

The entire system is operated at or slightly higher than ambient pressure, but all or portions of the system may be operated at pressures higher than ambient pressure.

In a preferred embodiment, the buffer tank equilibrates physical and chemical properties of the VFA's and AE's before the VFA's and AE's enter into the biogasification reactor. Physical and chemical properties include, but are not limited to, temperature, pH, conductivity, nutrients and biochemical oxygen demand. The VFA's and AE's, which are equilibrated with respect to physical and chemical properties, react more efficiently with bacteria in the biogasification reactor, resulting in higher gas production rate and yields.

Any hydrolysis or methanogenesis means known in the art can be used in the present invention. These include, but are not limited to, acids, bases, enzymes and combinations of these. In a preferred embodiment, the hydrolysis and methanogenesis means are microorganisms.

Any anaerobic fermentation system, such as single phase, two-phase or multiple-phase anaerobic fermentation systems or processes known in the art can be used in the present invention, although modified two phase anaerobic systems, as described as being preferred herein, are expected to yield greater volumes of methane.

In a given embodiment, the concentration of hydrogen gas collected from the hydrolysis reactor(s) is between about 10% to about 60%, more preferably between about 20% to about 50% and most preferably about 35%.

In a given embodiment, the concentration of the methane gas collected from the biogasification reactor is between about 40% to about 80%, and more preferably between about 90% to about 97%.

The recirculation of liquid from the biogasification reactor to the hydrolysis reactor can be a continuous process, or the recirculation of liquid from the biogasification reactor to the hydrolysis reactor can be an intermittent process. The recirculation process can occur for any range of time periods, such as for at least one second, to at least one minute, to for at least eight or more hours. The liquid recirculation system may incorporate devices that prevent or substantially inhibit the movement of solids from one vessel or reactor to another, such as a screen, sieve, strainer, grate, filter or similar device, or combinations of such devices, and pumps to affect the movement of liquids and solids among and between the vessels and reactors, the design of which are known to those skilled in the art.

In a given embodiment, the biogasification reactor incorporates a material, or materials, having a high surface area to volume ratio, in order to serve as a surface for methanogenic bacterial culture attachment and growth.

Any active hydrolytic or methane producing mesophilic or thermophilic anaerobic digestion system can be used in the present invention.

In one embodiment, hydrogen-producing anaerobic systems utilize microorganisms from the *Clostridium* species. For example, the *Clostridium* species may include, but may not be limited to, *C. thermolacticum, C. thermohydrosulfuricum, C. thermosucinogene, C. butyricum, C. botulinum, C. pasteurianum, C. thermocellum* and *C. beijirincki*. In a different embodiment, hydrogen-producing anaerobic systems utilize microorganisms from the *Lactobacillus* and/or the *Eubacteria* species. For example, the *Lactobacillus* species may include, but are not limited to, *Lactobacillus paracasel*, and/or the *Eubacteria* species may include, but are not limited to, *Eubacteria aerogenes*.

Preferred hydrolytic organisms include *Clostridium, Bacteroides, Ruminococcus, Acetivibrio, Lactobacillus* and other *Firmicutes* and *Proteobacteria*.

Methane-producing anaerobic systems utilizing acid forming bacteria and methane-producing organisms, as are well known to be employed to produce methane from sewage sludge or from brewery waste, can be employed in the practice of the present invention. A review of the microbiology of anaerobic digestion is set forth in "Anaerobic Digestion, 1. The Microbiology of Anaerobic Digestion," by D. F. Toerien and W. H. J. Hattingh, Water Research, Vol. 3, pages 385-416, Pergamon Press (1969). As noted therein, the principal suitable acid forming species include species from genera such as, but not limited to, *Aerobacter, Aeromonas, Alcaligenes, Bacillus, Bacteroides, Clostridium, Escherichia, Klebsiella, Leptospira, Micrococcus, Neiseria, Paracolobacterium, Proteus, Pseudomonas, Rhodopseudomonas, Rhodobacter sphaeroides, Rubrobacter* species, *Erythrobacter litoralis, Jannaschia* sp., *Rhodopirellula baltica, Sarcina, Serratia, Streptococcus* and *Streptomyces*. Also of use in the present invention are microorganisms which are selected from the group consisting of *Methanobacterium oinelianskii, Mb. Formicium, Mb. Sohngenii, Methanosarcina barkeri, Ms. Acetovorans, Ms. Methanica* and *Mc. Mazei, Methanobacterium thermoautotrophicus, Methanobacterium bryantii, Methanobrevibacter smithii, Methanobrevibacter arboriphilus, Methanobrevibacter ruminantium, Methanospirillum hungatei, Methanococcoides buntonii, Methanococcus vannielli, Methanothrix soehngenii Opfikon, Methanothrix* sp., *Methanosarcina mazei, Methanosarcina thermophila* and mixtures thereof.

Preferred methanogenic organisms include *Methanobacteriaceae, Methanosarcinaceae, Methanosaetaceae, Methanocorpusculaceae, Methaanomicrobiaceae* and other archaea organisms.

Other useful microorganisms and mixtures of microorganisms will be apparent to those of skill in the art.

For example, U.S. Pat. No. 6,543,535 and U.S. Published Application 2006/0254765 disclose representative microorganisms and nutrients, and the teachings thereof are incorporated by reference. Suitable stimulants may also be included.

Various chemical agents can be utilized in conjunction with such organisms to facilitate the growth of these organisms and thereby facilitate the methods of the invention. Such agents include, but are not limited to, major nutrients, vitamins, trace elements (for example, B, Co, Cu, Fe, Mg, Mn, Mo, Ni, Se, W, Zn as a non-limiting group) and buffers (such as phosphate and acetate buffers). Suitable growth media may also be included. In practicing the invention, it may be necessary to first determine the nature of the microbial consortium present in the coal deposit in order to determine the optimum growth conditions to be used as part of the inventive process.

A wide variety of substrates are utilized by methane producing bacteria but each species is currently believed to be characteristically limited to the use of a few compounds. Therefore, several species of methane producing bacteria may be required for complete fermentation of the compounds present in certain organic substrates, such as sewage or brewery waste. For example, the complete fermentation of valeric acid requires as many as three species of methane producing bacteria. Valeric acid is oxidized by *Mb. Suboxydans* to acetic and propionic acids, which are not attacked further by this organism. A second species, such as *Mb. Propionicum*, can convert the propionic acid to acetic acid, carbon dioxide and methane. A third species, such as *Methanosarcina methanica*, is required to ferment acetic acid.

The effluent from the biogasification phase of the two-phase anaerobic fermentation system may also be hydrolyzed in the pre-treatment phase of the system, or can be hydrolyzed in a biological process.

In one example, the organic substrate is Louisiana Wilcox formation lignite. Previous research has demonstrated the feasibility of anaerobically digesting this lignite, using a conventional single-stage stirred tank anaerobic fermentation reactor (Isbister, J. D. and Barik, S., Microbial Transformations of Low Rank Coals, pp 139-156. On the basis of its dry weight and via ultimate analysis, this lignite coal is approximately 63% carbon, 4.5% hydrogen, 1.3% nitrogen, 1.2% sulfur, 16% oxygen and 14% ash. Because a C/N ratio of about 25-35 is needed for good anaerobic digestion, nitrogen is supplemented, and can be added in inorganic forms, such as ammonia, or in organic forms such as nitrogen contained in food wastes, animal manure or urea.

In a preferred embodiment, the solubilized coal substrate is supplemented with a nitrogen source, and the nitrogen source is a member selected from the group consisting of animal manure, food waste, urea, inorganic nitrogen fertilizers, ammonia and combinations thereof.

In another aspect, the present invention uses a combined mechanical, chemical and anaerobic process system for hydrogen and methane production. This system comprises a coal grinding unit and gravity separation system, chemical pre-treatment system including at least one pre-treatment vessel, at least one hydrolysis reactor, a buffer tank and a biogasification reactor. The coal grinding unit includes a mechanical system that grinds, shears or pulverizes coal, and a conveyor or other transport method to deliver the coal to a gravity separation system. The gravity separation system may include any of several types of equipment that are capable to separating coal particles of a specific gravity range from non-coal particles having a different specific gravity range. The range of various designs of the coal grinding and gravity separation systems will be apparent to those of skill in the art.

The chemical pretreatment system has at least one vessel that contains a number of chemicals that are capable of solubilizing coal. The present system utilizes at least three vessels having one or more solids and liquid inlets and outlets, and at least one bottom outlet, and mechanical and/or hydraulic and/or magnetic means of stirring, agitation or blending, and that chemically treat the coal in steps. The chemical treatment in each vessel, or step, may include the addition of one or more chemicals, along with water, together or in sequence, and the mixture are stirred, blended, agitated or otherwise brought into robust contact with the coal for some period of time necessary for the desired chemical reactions to take place. Following chemical treatment in one vessel, the contents of the treatment vessel may be transferred to a second vessel for treatment with a different chemical or chemicals, along with water, and the mixture may be stirred, blended or agitated in order to provide for efficient reaction between the mixture and the chemicals. Following chemical treatment in the second vessel, the contents of the second treatment vessel are transferred to a third vessel for treatment with yet a different chemical or chemicals, with or without the addition of water, and the mixture may be stirred, blended or agitated in order to provide for efficient reaction between the mixture and the chemicals. Additional treatment steps are optionally incorporated in the pretreatment process to solubilize the coal. The chemical pretreatment system may also be arranged such that coal solids from any treatment vessel may be transferred to a previous or subsequent treatment vessel. Following pretreatment, the solubilized coal liquids are transferred to the hydrolysis reactor.

in a preferred embodiment, the hydrolysis reactor has at least one liquid inlet, at least one side liquid outlet and at least one outlet for gas produced in the hydrolysis vessel, such as methane, carbon dioxide, hydrogen and combinations thereof. The buffer tank also has at least one liquid inlet, at least one liquid outlet and at least one outlet for gas produced by the hydrolysis feed mixture in the buffer tank, such as methane, carbon dioxide, hydrogen and combinations thereof. Similarly, the biogasification reactor has at least one liquid inlet, at least one liquid outlet and at least one outlet for gas produced by the hydrolysis feed mixture in the buffer tank, such as methane, carbon dioxide, hydrogen and combinations thereof.

A preferred embodiment system utilizes transfer of the liquid from a hydrolysis tank, which contains VFA's and AE's, through one or more openings on the side wall of the hydrolysis tank using a solid-liquid separation device, which results in transfer of the substantially liquid hydrolysis feed solution into the buffer tank. The content of the hydrolysis feed solution on a weight/weight basis is preferred to be at least 80% liquid, and more preferably less than 5% solids.

Inlets and outlets of the hydrolysis, buffer and biogasification reactors are located so as to result in optimized working volume capacities of the vessels. Equipment capital cost and process efficiency are directly proportional to the working capacities of the vessels in a process system. In the preferred embodiment, the hydrolysis vessel(s) contain(s) a mixture of solubilized coal feedstock and an aqueous liquid to at least 50%, and more preferably at least 95% of the internal capacity of the hydrolysis vessel(s).

In a preferred embodiment, the hydrolysis feed solution is transferred from a hydrolysis vessel into a buffer tank where it is equilibrated with another hydrolysis feed solution from a different hydrolysis vessel. Equilibration of the hydrolysis feed solutions from two or more hydrolysis vessels minimizes sudden changes in VFA and AE concentration, pH and liquid content occurring when the hydrolysis feed solution is transferred directly from the hydrolysis vessel into the biogasification reactor. The equilibration of the hydrolysis feed solutions stabilizes the biogasification reactor and enhances the amount of gas formed by the reactor.

The hydrolysis reactor and the buffer tank are connected by a series of conduits through which liquid from one reactor can be transferred to the buffer tank. As such, the device also comprises a first conduit connecting the hydrolysis reactor outlet to the buffer tank inlet, a second conduit connecting the buffer tank outlet to the biogasification reactor inlet and a third conduit connecting the biogasification reactor outlet with the hydrolysis reactor inlet.

The volume capacities of the coal processor, coal separation unit, pretreatment system, hydrolysis reactor, the buffer tank and the biogasification tank are all variable depending upon the requirements of the application.

In a one embodiment, the system includes several hydrolysis reactors, with at least 12 or more hydrolysis reactors being preferred. Each hydrolysis reactor operates in batches or partial batches, while one or more biogasification reactors operate to produce gases continuously. In a different embodiment, the system may include several hydrolysis reactors operating continuously, with solutions entering and leaving the hydrolysis and biogasification reactors in continuous flow streams.

The pretreatment unit, the hydrolysis reactors, the buffer tank and the biogasification tank or tanks may be linked in fluid communication in any useful arrangement, such as parallel, series and combinations of parallel and series. In a preferred arrangement, each of the hydrolysis reactors is linked in parallel with the buffer tank, continuously or in batches feeding an aqueous solution of hydrolysis products such as VFA's and AE's into the buffer tank.

The contents of one or more of the pretreatment tank, the hydrolysis vessels, the buffer tank or the biogasification reactor can be agitated or stirred either continuously or periodically during the hydrolysis and biogasification process. Gas or motor driven stirrers, hydraulic stirrers, shakers, sonicators, magnetic stirrers, bubblers, homogenizers, or any other means known by one skilled in the art for agitation or stirring a liquid or suspension, can be used in the system of the invention.

Figure 1:
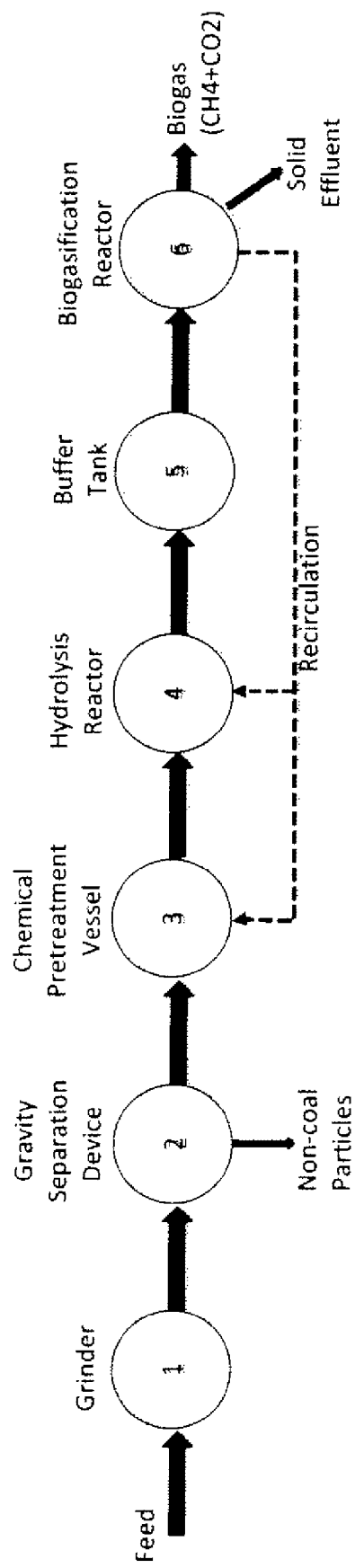
FIG. 1 is a diagram outlining an exemplary process of a system for coal bioconversion. In the diagram, a coal grinder is represented by the polygon numbered (1); a gravity separation device used to separate coal from non-coal materials is represented by the polygon numbered (2); one or more chemical pretreatment vessels are represented by the polygon numbered (3); a hydrolysis reactor is represented by the polygon numbered (4); a buffer tank is represented by the polygon numbered (5); and a biogasification reactor is represented by the polygon numbered (6).

FIG. 1 shows an example process for the production of hydrogen and methane gas. Feed coal is delivered to a mechanism 1 such as a grinder to reduce the coal particle size to a desired range. The coal particles are then fed into a gravity separation device 2, such as a float-sink tank or a hydrocyclone, whereby the non-coal particles are separated from the coal by differences in the specific gravities. The purified coal particles are then fed into one or more chemical pretreatment vessels 3, where the coal is combined with chemicals and water and the solution is stirred, agitated or otherwise mixed for a given period of time. The chemical pretreatment of the coal particles may involve several vessels and recirculation of solid coal particles between or among the vessels to complete the solubilization of the coal. The solubilized coal products are fed into one or more hydrolysis reactors 4. After a period of incubation in the hydrolysis reactor, hydrogen, methane and carbon dioxide gases are produced. The VFA's and AE's are then transferred from the hydrolysis reactor into the buffer tank 5. The hydrolysis feed solution from two or more hydrolysis vessels, containing VFA's and AE's, are equilibrated with the buffer tank. Hydrogen, methane and/or carbon dioxide may be generated in the buffer tank. The equilibrated hydrolysis mixture is transferred to a biogasification reactor 6. After a period of incubation in the biogasification reactor, methane, hydrogen and/or carbon dioxide gases are produced. Additionally, effluent in the biogasification reactor is filtered, with the resultant liquids returned to the solubilization tank. Following a period of incubation and digestion in the biogasification reactor, the resulting liquid in the biogasification reactor can be recirculated back into the chemical pretreatment vessel 3 via another conduit.

Figure 2:
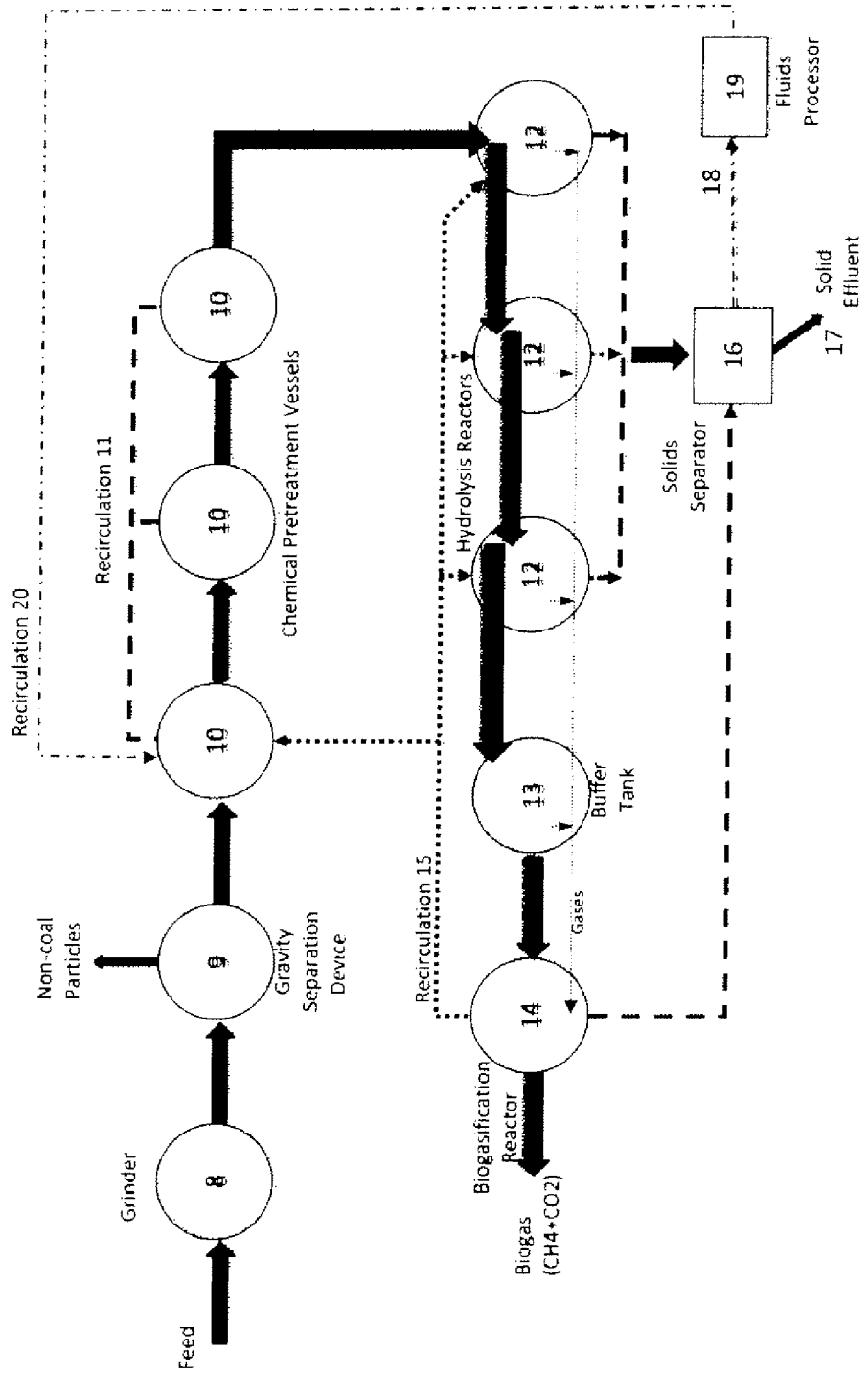
FIG. 2 is a diagram outlining an exemplary process of a system for coal bioconversion. In this diagram, a coal grinder is shown as the polygon numbered (8); a gravity separation device used to separate coal from non-coal materials is represented by the polygon numbered (9); chemical pretreatment vessels are represented by the polygons numbered (10); a recirculation line connecting the chemical pretreatment vessels is represented by the dotted line numbered (11); hydrolysis reactors are represented by the polygons numbered (12); a buffer tank is represented by the polygon numbered (13); a biogasification reactor is represented by the polygon numbered (14); a recirculation flow line connecting the biogasification reactor to one or more hydrolysis reactors is represented by the dotted line numbered (15); a solids separator is represented by a polygon numbered (16); solids effluent exiting the solids separator is represented by an arrow (17); fluids from the solids separator is represented by a dotted line (18)

A preferred embodiment of the invention for the production of methane and hydrogen gases from the device is shown in FIG. 2. Coal is pulverized 8 and delivered to a gravity separation unit 9 to remove non-coal particles. The purified coal particles are delivered into chemical pretreatment tanks 10, where the coal is solubilized. Coal solubilization may require multiple treatments and recirculation via the recirculation conduit 11. The solubilized coal product is delivered into the three hydrolysis reactors 12. After a period of incubation in the hydrolysis reactors, volatile fatty acids and/or acetates, and hydrogen and carbon dioxide gases are produced. The liquid containing the hydrolyzed substrate is then transferred from the hydrolysis reactors into the buffer tank 13 via a conduit. The hydrolysis solutions from the hydrolysis vessels are equilibrated with respect to their physical properties. Hydrogen, methane and/or carbon dioxide may be produced by the mixture in the buffer tank. The equilibrated hydrolysis solution is transferred to biogasification reactor 14 via a conduit. After a period of incubation in the biogasification reactor, hydrogen, methane and/or carbon dioxide gases are produced. Following a period of incubation and digestion in the biogasification reactor, cells in the remaining liquid can be retained and a portion of the liquid recirculated back into the either or both of the chemical pretreatment vessels or the three hydrolysis reactors via a different conduit 15. Residual material in the three hydrolysis reactors can be transferred from the three hydrolysis reactors to a solids separator 16 whereby solids and liquids are separated from each other. The solids 17 may be disposed of or may be put to beneficial use. The liquids 18 may be processed 19 to remove metals ions, salts and other contaminants, with the resultant water recirculated back to the chemical pretreatment tanks 20. Effluent from the biogasification reactor may be transferred to the solids separator 16.

EXAMPLE

A bench-scale system, consisting of a coal grinder, sieve and shaker table, chemical pre-treatment tank, hydrolysis tank, biogasification reactor, peristaltic pump, magnetic stir plates, tank heaters and manometer, was designed and constructed.

Pieces of lignite coal from the Dolet Hills coal mine, Mansfield, De Soto Parish, La., were ground in a OCG Systems Model 4E grinder. The ground coal was placed in a USA Standard Testing No. 60 sieve, and sieved to a size of 250 microns or less using a Retch Model AS200 shaker table. The sieved coal was then weighed, and 400 grams of coal particles were treated aerobically and abiotically in a 4 liter treatment vessel with chemical solutions in the following sequence:

1. A solution of 2 liters of 0.05 molar sodium hydroxide, stirred initially for 2-5 minutes and maintained at a constant temperature of 40° C. for 24 hours in a Blue M Dry Type Bacterialogical incubator;
2. The solution was then decanted and the supernatant was placed into a solution of 2 liters of 0.25 molar ethyl acetate, stirred initially for 2-5 minutes, and maintained at a constant temperature of 90° C. for 24 hours in a Blue M Dry Type Bacteriological incubator;
3. The solution was then decanted and the supernatant was placed into a solution of 0.4 liters of 0.9 molar hydrogen peroxide and 0.12 grams of iron chloride, initially hand-stirred for 2-5 minutes and maintained at a constant temperature of 40° C. for 48 hours in a Blue M Dry Type Bacteriological incubator. The iron chloride was added prior to the addition of the hydrogen peroxide. The pH was adjusted to 3.5 using a phosphate buffer prior to delivery to the hydrolysis tank.
4. The unsolubilized coal from each of the treatment steps was collected and placed back into the treatment vessel and the treatment steps were repeated until substantially all of the coal material was solubilized. The remaining solids were determined to be predominantly non-coal particles that were not removed via gravity separation prior to the chemical treatment.

The solubilized coal was delivered in increments into an 11.5 liter hydrolysis tank containing using a Master Flex Model No. 7519-25 peristaltic pump connecting the outlet of the chemical treatment tank to an inlet port on the side of the hydrolysis tank via 0.25 inch diameter clear flexible tubing. The headspace of the hydrolysis tank was initially purged and filled with nitrogen to a slight positive pressure of approximately 1 psig above ambient pressure. The fluid transfer was completed in increments of approximately 20% of the total solubilized coal volume, once per approximately 7 days. Upon completion of the fluid transfer from chemical treatment the tank to the hydrolysis tank, the pH of the fluids in the hydrolysis tank was measured with a pH meter, Thermo Model No. Orion 5 Star and adjusted to and maintained at approximately 5.5-6.0 via the addition of sodium bicarbonate.

The hydrolysis tank was constructed of clear acrylic resin in cylindrical shape, fitted with rubber top and bottom O-ring seals and affixed with stainless steel screws. The tank was fitted with multiple ports and valves to accommodate fluids and gases transfer and sampling, a Marineland Model No. Stealth 100W indirect submersible heater and the use of a Stir-Pak Model No. 50007-20 stirrer. A magnetic stir bar 60 mm in length was inserted in the hydrolysis tank and the tank was placed on a VMR Model No. 620-S magnetic stir plate. The tank was continuously stirred with the stir bar rotating at approximately 400 rpm.

Fluid and gas samples were collected several times daily using a syringe through sampling ports and analyzed for the presence of gases and chemicals that result from anaerobic fermentation, such as hydrogen gas and volatile fatty acids and acetate, as well as nutrients content, using a Varian 500-MS LC liquid chromatography/mass spectrometry instrument, and a Varian Model 320-MS triple quadrupole gas chromatography/mass spectrometry instrument. Total organic carbon content was measured using a Dionex ICS-3000 ion chromatography instrument. Each analyses were run in duplicates. After these gases and chemicals increased in concentration in the hydrolysis reactor over a period of approximately 6 days, a fluid volume equivalent to that transferred into the hydrolysis tank was transferred to the biogasification reactor using a Stenner Model No. 170DM5 peristaltic pump.

The biogasification reactor was also constructed of clear acrylic resin in cylindrical shape, fitted with rubber top and bottom O-ring seals and affixed with stainless steel screws. The tank was fitted with multiple ports and valves to accommodate fluids and gases transfer and sampling, and a Marineland Model No. Stealth 100W indirect submersible heater. A plastic mesh divider and approximately 30 Bioballs plastic biological filter media were placed into the reactor to provide a high surface area growth support for the methanogenic culture in the reactor. A magnetic stir bar 60 mm in length was inserted in the hydrolysis tank and the tank was placed on a VWR Model No. 620-S magnetic stir plate. Approximately 2 liters of solution comprised of water, nutrients and methanogenic anaerobes were placed into the tank. The tank was continuously stirred with the stir bar rotating at approximately 100 rpm.

Fluid volumes approximately equivalent to those periodically transferred into the hydrolysis tank, were transferred to the biogasification tank, just prior to each subsequent transfer of fluids from the chemical treatment tank to the hydrolysis tank. Upon completion of the fluid transfer from the hydrolysis tank to the biogasification tank, the pH of the fluids in the biogasification tank was measured with a pH meter, Thermo Scientific Orion 5 Star pH/ISE/Conductivity/DO Benchtop meter and adjusted to and maintained at approximately 7.5 via the addition of sodium bicarbonate.

Methane and carbon dioxide gases were produced from the biogasification tank through a valve on the top of the tank connected by clear plastic tubing to a manometer apparatus. The manometer apparatus allows for collection of the produced gases and direct measurement of the total gas volume produced by displacement of a column of water. A sampling port on the gas outlet valve enabled daily sampling with a syringe. The sampled gases were analyzed for composition with a Varian Model GC-500 gas chromatograph. Samples of the fluids in the biogasification tank were collected daily and analyzed for the presence of volatile fatty acids and acetate and nutrients content using a Varian 500-MS LC liquid chromatography/mass spectrometry instrument, and a Varian Model 320-MS triple quadrupole gas chromatography/mass spectrometry instrument. Each analyses were run in duplicates. Production of gases from the biogasification tank were monitored and recorded for a total period of approximately 90 days, as additional volumes of fluids from the hydrolysis tank were transferred into the biogasification reactor approximately every 7 days.

Data Analysis

Actual biogas yields were calculated from the gas composition and the total headspace, where the total headspace is equal to the headspace in the reactor and the amount of gas in the manometer. The actual biogas yield also assumed gas temperature of 40° C. and atmospheric pressure of 0.833 atm. The standard volume of gas was determined by ideal gas law relationship $$V_s = P_a V_a T_s / T_a P_s$$

where,
$V_a$=standard gas volume
$V_a$=actual gas volume
$T_a$=actual gas temperature
$T_s$=standard gas temperature (273 K)
$P_a$=actual gas pressure
$P_s$=standard gas pressure (1 atm)

Based on the coal amount that was liquefied in the pretreatment and the amount transferred to stage II, the volume of gas was extrapolated to a scf/ton coal basis. The fraction of the amount of coal consumed for gas production was calculated using a stoichiometric relationship of the amount of carbon in coal (i.e., on a mole carbon basis) assuming ~65% of coal is carbon. Gas volume calculations were corrected for loss or dilution due to gas collection and water sampling.

Results and Discussion

The criteria for the performance of this system was total biogas production, the composition of the produced biogas, and the percent of the feedstock coal that was converted to biogas. The system was operated in batch mode, with periodic transfers of approximately 20% of the solubilized coal volume from the chemical pretreatment tank to the hydrolysis tank, and concomitant transfers of approximately equivalent volumes of fluids from the hydrolysis tank to the biogasification tank.

Daily monitoring and adjustments of pH helped maintain consistent system operation in the reactor vessels.

Biogas production began within approximately 16 hours following transfer of fluids containing VFA's and acetate from the hydrolysis tank, and increased steadily over a 60-day operation period of the system. Biogas production then stabilized for a period of 17 days, before tapering off for the remaining 14 days of system operation. The pH was monitored daily in the hydrolysis and biogasification reactors and adjusted periodically to maintain the desired pH in each. Over the operation period, the pH in the hydrolysis reactor varied as hydrolysis proceeded following each solubilized coal transfer from the chemical treatment tank, requiring regular additions of sodium hydroxide to raise the pH to the desired level. FIG. 3 is a plot of the pH of the hydrolysis vessel and the biogasification reactor, measured daily. The cumulative biogas and methane production rates from the biogasification reactor are shown in FIG. 4. The daily biogas and methane production from the biogasification reactor are shown in FIG. 5.

Solubilized coal was measured based on the carbon contents in the solid and aqueous phases (e.g., weight, total COD, TOC) organic acids were analyzed with the LC-MS. FIG. 6 is a plot of percent of total organic acid present in the hydrolysis reactor of the COMCAPS system. FIG. 7 is a plot of percent of remaining dissolved coal carbon in the hydrolysis reactor of the COMCAPS system.

Acetate, total organic acids, COD, A450 were monitored frequently during the system operation.

Conclusions

The COMCAPS system was evaluated for its ability to convert coal to methane gas under constant 40° C. thermophilic conditions. Lignite was crushed, sieved, and treated with a series of chemicals, and the solubilized coal liquids were transferred in approximate 20% increments to a hydrolysis phase anaerobic vessel, where a hydrolytic bacterial culture converted the solubilized coal product to predominantly VFA's and acetate. After a period of time, an approximately equivalent volume of the solution in the hydrolysis phase vessel was transferred to the biogasification reactor, where methane, carbon dioxide and hydrogen were produced. The process continued as described herein until substantially all of the coal solids were solubilized, the solubilized coal products were hydrolyzed, and the VFA's and acetates resulting from hydrolysis were converted to methane, carbon dioxide and hydrogen. Under these operating conditions. The cumulative methane yields after a period of 15 and 30 days were, respectively 17 L and 42 L. The soluble coal conversion at these same system operating time intervals was 26.5% and 61.4%. The concentration of organic acid remaining in the hydrolysis reactor at these time intervals was 1490 and 1965 mg/L.

All publications, patents and patent applications mentioned in this specification are herein incorporated by reference into the specification to the same extent as if each individual publication, patent or patent application was specifically and individually indicated to be incorporated herein by reference.

What is claimed is:

1. A process for converting coal ex situ, comprising:
   (a) treating coal with a liquid that solubilizes at least a portion of the coal to form a product that is a substrate for a hydrolytic microbial population,
   (b) treating at least a portion of the product of step (a) with the hydrolytic microbial population to produce a product containing fatty acids or fatty acid esters, and
   (c) treating at least a liquid portion of the product from step (b) with an anaerobic microbial population that generates methane to produce a product containing methane, wherein steps (a), (b) and (c) are performed separately.

2. The process of claim 1, wherein steps (a), (b) and (c) are performed in different vessels.

3. The process of claim 1, wherein the coal used in step (a) is pulverized coal.

4. The process of claim 1, wherein the coal used in step (a) is coal that has been treated to remove at least a portion of non-coal impurities.

5. The process of claim 1, wherein step (a) comprises the steps of:
   (i) treating coal with an alkali;
   (ii) treating coal with a $C_1$-$C_4$ carboxylic acid, benzoic acid, or salt or ester of such acid, or a combination thereof; and
   (iii) treating coal with hydrogen peroxide in the presence of iron, and wherein the order of such steps is not essential.

6. The method of claim 5, wherein said alkali is sodium hydroxide or potassium hydroxide.

7. The process of claim 1, wherein the hydrolytic microbial population of step (b) includes an acetogen.

8. The process according to claim 1, wherein the anaerobic process may consist of a single phase, two phases or more than two phases of hydrolysis and biogasification.

9. The process of claim 1, wherein more than one hydrolysis phase vessel is utilized.

10. The process of claim 1, wherein more than one biogasification phase vessel is utilized.

11. The process of claim 1, wherein the coal is lignite, sub-bituminous coal, bituminous coal, semi-anthracite coal, anthracite coal or a combination thereof.

12. The process according to claim 1, wherein said hydrolytic microbial population of step (b) is a member selected from the group consisting of *Acetivibrio, Clostridium, Lactobacillus, Ruminococcus, Zootermopsis*, and other *Firmicutes, Proteobacteria* and a combination of these.

13. The process of claim 1, wherein said microbial population of step (c) is a member selected from the group consisting of *Aerobacter, Aeromonas, Alcaligenes, Bacillus, Bacteroides, Clostridium, Escherichia, Klebsiella, Leptospira, Micrococcus, Neisseria, Paracobacterium, Proteus, Pseudomonas, Rhodopseudomonas, Sarcina, Serratia, Streptococcus* and *Streptomyces, Methanobaeterium omelianskii, Mb. Formieium, Mb. Sohngenii, Methanosarcina barkeri, Ms. Methaniea, Me. Masei, Methanobaeterium the rmoautotrophieum, Methanobaeterium bryantii, Methanobrevibaeter smithii, Methanobrevibaeter arboriphilus, Methanobrevibaeter ruminantium, Methanospirillum hungatei, Methanoeoeeus vannie iii, Methanothrix soehngenii, Methanothrix sp., Methanosareina mazei, Methanosareina thermophila, Methanobaeteriaeeae, Methanosareinaeeae, Methanosaetaeeae, Methanoeorpuseulaeeae, Methaanomierobiaeeae,* other arehaea and a combination of these.

14. The process of claim 1, wherein one or more of said treating steps is performed in a tank, hydrolysis vessel or bioreactor that is agitated, stirred or mixed either continuously or intermittently.

15. The process of claim 1, wherein step (c) occurs in a container that contains within it a material that provides a medium for growth of methanogenic bacteria and which provides a surface area for said growth.

16. The process of claim 1, including a device to separate the effluent solids and liquids from a biogasification reactor, such that the solids may be disposed of or put to a beneficial use, and such that the liquids may be further treated, if necessary, and recycled to a chemical pretreatment tank.

17. The process of claim 1, wherein the anaerobic microbial population of step (c) includes methanogenic bacterial cells.

18. The process of claim 17, wherein the methanogenic bacterial cells are separated from the effluent liquid and solids and retained within a reactor.

19. The process of claim 1, wherein the liquid of step (a) fs includes acridine, anthracene, fluorene, chrysene, fluoranthene, pyrene or catechol.

20. The process of claim 1, wherein the liquid of step (a) includes a member selected from an alkali, a carboxylic acid, a salt of a carboxylic acid, an ester of a carboxylic acid, phosphorous acid, an ester of phosphorous acid, phosphoric acid, an ester of phosphoric acid and a peroxide.

21. The process of claim 20, wherein said liquid is an alkali.

22. The process of claim 21, wherein said alkali is NaOH or KOH.

23. The process of claim 21, wherein said alkali is a Lewis base.

24. The process of claim 20, wherein said member is a $C_1$-$C_4$ carboxylic acid, a salt of a $C_1$-$C_4$ carboxylic acid or an ester of a $C_1$-$C_4$ carboxylic acid.

25. The process of claim 24, wherein said member is acetic acid or a salt or ester of acetic acid.

26. The process of claim 20, wherein said member is phosphorous acid or an ester of phosphorous acid.

27. The process of claim 20, wherein said member is a peroxide.

28. The process of claim 27, wherein said peroxide is hydrogen peroxide.

29. The process of claim 28, wherein said treatment is with hydrogen peroxide in the presence of iron.

30. The process of claim 1, wherein step (a) comprises the steps of:
   (i) treating coal with sodium hydroxide;
   (ii) treating at least a portion of the product from (i) with acetic acid or a salt or ester of acetic acid, and
   (iii) treating at least a portion of the product from (ii) with hydrogen peroxide in the presence of iron.

31. The process of claim 1, wherein the liquid of step (a) includes a member selected from the group consisting of aryl alcohols, metal ions, and phosphite esters.

32. The process of claim 1, wherein the liquid of step (a) includes a member selected from the group consisting of aryl alcohols, sodium hydroxide and hydrogen peroxide.

* * * * *

UNITED STATES PATENT AND TRADEMARK OFFICE
CERTIFICATE OF CORRECTION

| | | |
|---|---|---|
| PATENT NO. | : 9,102,953 B2 | Page 1 of 1 |
| APPLICATION NO. | : 12/965285 | |
| DATED | : August 11, 2015 | |
| INVENTOR(S) | : Robert A. Downey, Song Jin and Paul H. Fallgren | |

It is certified that error appears in the above-identified patent and that said Letters Patent is hereby corrected as shown below:

In the Claims

Column 19, line 55, claim 13, replace the word "Paracobacterium" with "Paracolobacterium."

Column 20, line 24, claim 19, please delete the word "fs."

Signed and Sealed this
Third Day of May, 2016

Michelle K. Lee
*Director of the United States Patent and Trademark Office*